US012780927B2

(12) United States Patent
Ford et al.

(10) Patent No.: US 12,780,927 B2
(45) Date of Patent: Nov. 3, 2026

(54) COMPOSITIONS AND METHODS FOR TREATING NONINFLAMMATORY PAIN IN SUBJECTS WITH RHEUMATOID ARTHRITIS

(71) Applicant: SANOFI BIOTECHNOLOGY, Paris (FR)

(72) Inventors: Kerri Ford, Bridgewater, NJ (US); Hubert Van Hoogstraten, Bridgewater, NJ (US)

(73) Assignee: SANOFI BIOTECHNOLOGY, Gentilly (FR)

( * ) Notice: Subject to any disclaimer, the term of this patent is extended or adjusted under 35 U.S.C. 154(b) by 1022 days.

(21) Appl. No.: 17/926,123

(22) PCT Filed: May 27, 2021

(86) PCT No.: PCT/IB2021/054652

§ 371 (c)(1),
(2) Date: Nov. 17, 2022

(87) PCT Pub. No.: WO2021/240436

PCT Pub. Date: Dec. 2, 2021

(65) Prior Publication Data

US 2023/0192871 A1 Jun. 22, 2023

Related U.S. Application Data

(60) Provisional application No. 63/077,378, filed on Sep. 11, 2020, provisional application No. 63/032,035, filed on May 29, 2020.

(30) Foreign Application Priority Data

May 11, 2021 (EP) .................................... 21315081

(51) Int. Cl.

| | |
|---|---|
| ***C07K 16/28*** | (2006.01) |
| ***A61K 39/395*** | (2006.01) |
| ***A61K 45/06*** | (2006.01) |
| ***A61P 19/02*** | (2006.01) |
| ***A61P 29/00*** | (2006.01) |
| ***C07K 14/715*** | (2006.01) |
| *A61K 39/00* | (2006.01) |

(52) U.S. Cl.

CPC .......... *C07K 16/2866* (2013.01); *A61K 45/06* (2013.01); *A61P 19/02* (2018.01); *A61P 29/00* (2018.01); *C07K 14/7155* (2013.01); *A61K 2039/505* (2013.01); *A61K 2039/54* (2013.01); *A61K 2039/545* (2013.01)

(58) Field of Classification Search

None

See application file for complete search history.

(56) References Cited

U.S. PATENT DOCUMENTS

| | | | |
|---|---|---|---|
| 4,997,423 | A | 3/1991 | Okuda et al. |
| 5,016,784 | A | 5/1991 | Batson |
| 5,215,534 | A | 6/1993 | De Harde et al. |
| 5,480,796 | A | 1/1996 | Kishimoto |
| 5,605,690 | A | 2/1997 | Jacobs et al. |
| 5,670,373 | A | 9/1997 | Kishimoto |
| 5,723,120 | A | 3/1998 | Brackenhoff et al. |
| 5,795,965 | A | 8/1998 | Tsuchiya |
| 5,817,790 | A | 10/1998 | Tsuchiya |
| 5,888,510 | A | 3/1999 | Kishimoto |
| 5,888,511 | A | 3/1999 | Skurkovich et al. |
| 5,908,686 | A | 6/1999 | Sudo et al. |
| 6,046,223 | A | 4/2000 | Sponsel et al. |
| 6,086,874 | A | 7/2000 | Yoshida et al. |
| 6,261,560 | B1 | 7/2001 | Tsujinaka et al. |
| 6,286,699 | B1 | 9/2001 | Sudo |
| 6,410,691 | B1 | 6/2002 | Kishimoto |
| 6,629,949 | B1 | 10/2003 | Douglas et al. |
| 6,632,927 | B2 | 10/2003 | Adair |
| 6,645,635 | B2 | 11/2003 | Murakai |
| 6,659,982 | B2 | 12/2003 | Douglas et al. |
| 6,670,373 | B1 | 12/2003 | Bonjouklian et al. |
| 6,692,742 | B1 | 2/2004 | Nakamura et al. |
| 6,723,319 | B1 | 4/2004 | Ito et al. |
| 7,226,554 | B2 | 6/2007 | Sudo et al. |
| 7,320,792 | B2 | 1/2008 | Ito et al. |
| 7,479,543 | B2 | 1/2009 | Tsuchiya et al. |
| 7,521,052 | B2 | 4/2009 | Okuda et al. |
| 7,582,298 | B2 | 9/2009 | Stevens et al. |
| 8,043,617 | B2 | 10/2011 | Stevens et al. |
| 8,080,248 | B2 | 12/2011 | Radin |
| 8,183,014 | B2 | 5/2012 | Stevens et al. |
| 8,192,741 | B2 | 6/2012 | Radin |

(Continued)

FOREIGN PATENT DOCUMENTS

| | | |
|---|---|---|
| BR | PI0712224-1 A2 | 1/2012 |
| CN | 103476793 A | 12/2013 |

(Continued)

OTHER PUBLICATIONS

Kevzara® FDA Label revised Apr. 2018, 49 pages.*
U.S. Appl. No. 13/648,521 2013/0149310 U.S. Pat. No. 9,943,594, filed Oct. 10, 2012 Jun. 13, 2013 Apr. 17, 2018, Martine Jasson, Methods for the Treatment of Rheumatoid Arthritis.
U.S. Appl. No. 14/350,973 2014/0302053 U.S. Pat. No. 10,927,435, filed Apr. 10, 2014 Oct. 9, 2014 Feb. 23, 2021, Xiaohong Huang, Compositions for the Treatment of Rheumatoid Arthritis and Methods of Using Same.
U.S. Appl. No. 17/133,870 2021/0230719, filed Dec. 24, 2020 Jul. 29, 2021, Xiaohong Huang, Compositions for the Treatment of Rheumatoid Arthritis and Methods of Using Same.

(Continued)

*Primary Examiner* — Ilia I Ouspenski
(74) *Attorney, Agent, or Firm* — LATHROP GPM LLP; James H. Velema, Esq.; Judith L. Stone-Hulslander, Esq.

(57) ABSTRACT

The present disclosure relates to the use of an anti-IL6 receptor antibody for treating non-inflammatory pain in subjects with rheumatoid arthritis.

23 Claims, 2 Drawing Sheets

Specification includes a Sequence Listing.

(56) References Cited

U.S. PATENT DOCUMENTS

| | | | |
|---|---|---|---|
| 8,440,890 | B1 | 5/2013 | Carlone, Jr. et al. |
| 8,568,721 | B2 | 10/2013 | Radin |
| 8,709,409 | B2 | 4/2014 | Okuda et al. |
| 8,869,904 | B2 | 10/2014 | Jani |
| 8,895,521 | B2 | 11/2014 | Klinman et al. |
| 9,139,646 | B2 | 9/2015 | Solinger et al. |
| 9,173,880 | B2 | 11/2015 | Dix et al. |
| 9,248,242 | B2 | 2/2016 | Verespej et al. |
| 9,308,256 | B2 | 4/2016 | Radin et al. |
| 9,427,531 | B2 | 8/2016 | Hourmand et al. |
| 9,566,395 | B2 | 2/2017 | Denny et al. |
| 9,884,916 | B2 | 2/2018 | Stevens et al. |
| 9,943,594 | B2 | 4/2018 | Jasson et al. |
| 9,951,130 | B2 | 4/2018 | Schmidt et al. |
| 10,072,086 | B2 | 9/2018 | Dix et al. |
| 10,231,981 | B2 | 3/2019 | Zhang et al. |
| 10,927,435 | B2 | 2/2021 | Huang et al. |
| 10,968,278 | B2 | 4/2021 | Sridhara Sundaram et al. |
| 11,498,969 | B2 | 11/2022 | Baret-Cormel et al. |
| 12,297,279 | B2 | 5/2025 | Boklage et al. |
| 2002/0187150 | A1 | 12/2002 | Mihara et al. |
| 2003/0092606 | A1 | 5/2003 | L'Italien et al. |
| 2003/0113316 | A1 | 6/2003 | Kaisheva et al. |
| 2003/0190316 | A1 | 10/2003 | Katuka et al. |
| 2004/0071706 | A1 | 4/2004 | Ito et al. |
| 2004/0115197 | A1 | 6/2004 | Yoshizaki et al. |
| 2004/0197324 | A1 | 10/2004 | Liu et al. |
| 2004/0202658 | A1 | 10/2004 | Benyunes |
| 2004/0219156 | A1 | 11/2004 | Goldenberg et al. |
| 2005/0142635 | A1 | 6/2005 | Tsuchiya et al. |
| 2005/0238644 | A1 | 10/2005 | Mihara et al. |
| 2006/0078531 | A1 | 4/2006 | Sota |
| 2006/0078532 | A1 | 4/2006 | Omoigui |
| 2006/0078533 | A1 | 4/2006 | Omoigui |
| 2006/0177436 | A1 | 8/2006 | Ghilardi et al. |
| 2006/0251653 | A1 | 11/2006 | Okuda et al. |
| 2006/0275294 | A1 | 12/2006 | Omoigui |
| 2006/0292147 | A1 | 12/2006 | Yoshizaki et al. |
| 2007/0036785 | A1 | 2/2007 | Kishimoto et al. |
| 2007/0036788 | A1 | 2/2007 | Sheriff et al. |
| 2007/0098714 | A1 | 5/2007 | Nishimoto et al. |
| 2007/0143168 | A1 | 6/2007 | Stevens et al. |
| 2007/0148169 | A1 | 6/2007 | Yoshizaki et al. |
| 2007/0280945 | A1 | 12/2007 | Stevens |
| 2008/0124325 | A1 | 5/2008 | Ito et al. |
| 2008/0131374 | A1 | 6/2008 | Medich et al. |
| 2008/0145367 | A1 | 6/2008 | Bove et al. |
| 2008/0269467 | A1 | 10/2008 | Allan et al. |
| 2009/0082288 | A1 | 3/2009 | Klinman et al. |
| 2010/0316627 | A1 | 12/2010 | Stevens et al. |
| 2010/0316636 | A1 | 12/2010 | Radin et al. |
| 2011/0098450 | A1 | 4/2011 | Igawa et al. |
| 2011/0171241 | A1 | 7/2011 | Dix et al. |
| 2011/0245473 | A1 | 10/2011 | Igawa et al. |
| 2012/0003697 | A1 | 1/2012 | Stevens et al. |
| 2012/0171123 | A1 | 7/2012 | Medich et al. |
| 2012/0258098 | A1 | 10/2012 | Radin et al. |
| 2012/0301460 | A1 | 11/2012 | Bao et al. |
| 2013/0014958 | A1 | 1/2013 | Jani |
| 2013/0149310 | A1 | 6/2013 | Jasson et al. |
| 2014/0255390 | A1 | 9/2014 | Radin et al. |
| 2014/0302053 | A1 | 10/2014 | Huang et al. |
| 2015/0050277 | A1 | 2/2015 | Peters et al. |
| 2016/0002341 | A1 | 1/2016 | Dix et al. |
| 2016/0220675 | A1 | 8/2016 | Abrahmson |
| 2016/0229916 | A1 | 8/2016 | Stevens et al. |
| 2016/0280782 | A1 | 9/2016 | Huang et al. |
| 2016/0281106 | A1 | 9/2016 | Kim et al. |
| 2017/0166646 | A1 | 6/2017 | Sridhara Sundaram et al. |
| 2017/0198045 | A1 | 7/2017 | Johnson et al. |
| 2017/0252434 | A1 | 9/2017 | Joseph et al. |
| 2017/0360807 | A1 | 12/2017 | Zhang et al. |
| 2018/0296670 | A1 | 10/2018 | Jasson et al. |
| 2019/0002574 | A1 | 1/2019 | Dix et al. |
| 2019/0100585 | A1 | 4/2019 | Bauer et al. |
| 2020/0047029 | A1 | 2/2020 | Bentley et al. |
| 2020/0339693 | A1 | 10/2020 | Baret-Cormel et al. |
| 2020/0399380 | A1 | 12/2020 | Boklage et al. |
| 2020/0405851 | A1 | 12/2020 | Boyapati et al. |
| 2021/0230719 | A1 | 7/2021 | Huang et al. |
| 2021/0240369 | A1 | 8/2021 | Cain |
| 2021/0301027 | A1 | 9/2021 | Sridhara Sundaram et al. |
| 2022/0242959 | A1 | 8/2022 | Chen et al. |
| 2023/0127528 | A1 | 4/2023 | Baret-Cormel et al. |
| 2023/0174657 | A1 | 6/2023 | Albrecht et al. |
| 2023/0193871 | A1 | 6/2023 | Ford et al. |
| 2025/0333522 | A1 | 10/2025 | Boklage et al. |
| 2026/0027202 | A1 | 1/2026 | Jasson et al. |

FOREIGN PATENT DOCUMENTS

| | | | |
|---|---|---|---|
| CN | 104105505 | A | 10/2014 |
| CN | 104903349 | A | 9/2015 |
| CN | 102869346 | A | 1/2023 |
| EA | 014226 | B1 | 10/2010 |
| EA | 014298 | B1 | 10/2010 |
| EP | 0628639 | A1 | 12/1994 |
| EP | 0409607 | B1 | 10/1996 |
| EP | 0783893 | A1 | 7/1997 |
| EP | 0800829 | A1 | 10/1997 |
| EP | 0811384 | A2 | 12/1997 |
| EP | 0923941 | A2 | 6/1999 |
| EP | 1004315 | A1 | 5/2000 |
| EP | 1074268 | A1 | 2/2001 |
| EP | 1108435 | A1 | 6/2001 |
| EP | 1314437 | A1 | 5/2003 |
| EP | 1327681 | A1 | 7/2003 |
| EP | 1475100 | A1 | 11/2004 |
| EP | 1475101 | A1 | 11/2004 |
| EP | 0413908 | B2 | 8/2005 |
| EP | 1810980 | A1 | 7/2007 |
| EP | 1334731 | B1 | 2/2008 |
| EP | 2451438 | B1 | 2/2014 |
| EP | 2766039 | A1 | 8/2014 |
| EP | 3071230 | A1 | 9/2016 |
| EP | 3193934 | A1 | 7/2017 |
| EP | 3371224 | A1 | 9/2018 |
| EP | 3426295 | A1 | 1/2019 |
| EP | 3770173 | A1 | 1/2021 |
| EP | 3983071 | A1 | 4/2022 |
| FR | 2694767 | A1 | 2/1994 |
| JP | 2009-539349 | A | 11/2009 |
| JP | 2014-530226 | A | 11/2014 |
| JP | 61-22018 | B2 | 4/2017 |
| JP | 2017-137338 | A | 8/2017 |
| JP | 63-36171 | B2 | 5/2018 |
| JP | 2020-045351 | A | 3/2020 |
| RU | 2358762 | C2 | 6/2009 |
| TW | 201141518 | A | 12/2011 |
| WO | WO 1992/016553 | A1 | 10/1992 |
| WO | WO 1992/019759 | A1 | 11/1992 |
| WO | WO 1994/006476 | A1 | 3/1994 |
| WO | WO 1995/009873 | A1 | 4/1995 |
| WO | WO 1996/011020 | A1 | 4/1996 |
| WO | WO 2002/100330 | A2 | 12/2002 |
| WO | WO 2003/009817 | A2 | 2/2003 |
| WO | WO 2004/039826 | A1 | 5/2004 |
| WO | WO 2004/091658 | A1 | 10/2004 |
| WO | WO 2004/096273 | A1 | 11/2004 |
| WO | WO 2005/028514 | A1 | 3/2005 |
| WO | WO 2005/058365 | A1 | 6/2005 |
| WO | WO 2005/016280 | A2 | 2/2006 |
| WO | WO 2006/033702 | A2 | 3/2006 |
| WO | WO 2006/125229 | A2 | 11/2006 |
| WO | WO 2007/062040 | A1 | 5/2007 |
| WO | WO 2007/070750 | A1 | 6/2007 |
| WO | WO 2007/143168 | A2 | 12/2007 |
| WO | WO 2007/147001 | A2 | 12/2007 |
| WO | WO 2008/020079 | A1 | 2/2008 |
| WO | WO 2008/049897 | A1 | 5/2008 |
| WO | WO 2008/145142 | A1 | 12/2008 |
| WO | WO 2009/095489 | A2 | 8/2009 |
| WO | WO 2009/109584 | A1 | 9/2009 |
| WO | WO 2009/125825 | A1 | 10/2009 |

(56) References Cited

FOREIGN PATENT DOCUMENTS

| | | | |
|---|---|---|---|
| WO | WO 2009/140348 | A2 | 11/2009 |
| WO | WO 2010/035769 | A1 | 4/2010 |
| WO | WO 2010/106812 | A1 | 9/2010 |
| WO | WO 2010/149771 | A1 | 12/2010 |
| WO | WO 2011/085158 | A2 | 7/2011 |
| WO | WO 2012/064627 | A2 | 5/2012 |
| WO | WO 2013/053751 | A1 | 4/2013 |
| WO | WO 2013/056751 | A1 | 4/2013 |
| WO | WO 2015/077582 | A1 | 5/2015 |
| WO | WO 2015/148790 | A1 | 10/2015 |
| WO | WO 2016/044343 | A1 | 3/2016 |
| WO | WO 2017/038986 | A1 | 3/2017 |
| WO | WO 2017/079443 | A1 | 5/2017 |
| WO | WO 2017/106312 | A1 | 6/2017 |
| WO | WO 2017/155990 | A1 | 9/2017 |
| WO | WO 2017/194779 | A1 | 11/2017 |
| WO | WO 2018/007442 | A1 | 1/2018 |
| WO | WO 2020/047029 | A1 | 3/2020 |
| WO | WO 2020/160465 | A1 | 8/2020 |
| WO | WO 2020/219960 | A1 | 10/2020 |
| WO | WO 2020/247461 | A1 | 12/2020 |
| WO | WO 2020/252214 | A1 | 12/2020 |
| WO | WO 2021/240436 | A1 | 12/2021 |

OTHER PUBLICATIONS

U.S. Appl. No. 15/910,733 2018/0296670, filed Mar. 2, 2018 Oct. 18, 2018, Martine Jasson, Treatment of Rheumatoid Arthritis With an IL-6R Antibody.

U.S. Appl. No. 15/034,531 2016/0280782, filed May 4, 2016 Sep. 29, 2016, Xiaohong Huang, Compositions for the Treatment of Rheumatoid Arthritis and Methods of Using Same.

U.S. Appl. No. 15/505,056 2017/0252434, filed Feb. 17, 2017 Sep. 7, 2017, George Johny Joseph, Methods for Improving Sleep of Rheumatoid Arthritis Patients.

U.S. Appl. No. 15/342,833 2017/0166646 U.S. Pat. No. 10,968,278, filed Nov. 3, 2016 Jun. 15, 2017 Apr. 6, 2021, Preethi Aavali Sridhara Sundaram, Compositions Comprising IL-6R Antibodies for the Treatment of Uveitis and Macular Edema and Methods of Using Same.

U.S. Appl. No. 17/183,904 2021/0301027, filed Feb. 24, 2021 Sep. 30, 2021, Preethi Aavali Sridhara Sundaram, Compositions Comprising IL-6R Antibodies for the Treatment of Uveitis and Macular Edema and Methods of Using Same.

U.S. Appl. No. 16/082,841 2019/0100585, filed Sep. 6, 2018 Apr. 4, 2019, Deborah Bauer, Methods for Treating a Subject Suffering From Rheumatoid Arthritis.

U.S. Appl. No. 16/779,187 2020/0339693 U.S. Pat. No. 11,498,969, filed Jan. 31, 2020 Oct. 29, 2020 Nov. 15, 2022, Lydie Baret-Cormel, Compositions and Methods for Treating Juvenile Idiopathic Arthritis.

U.S. Appl. No. 17/934,259 2023/0127528, filed Sep. 22, 2022 Apr. 27, 2023, Lydie Baret-Cormel, Compositions and Methods for Treating Juvenile Idiopathic Arthritis.

U.S. Appl. No. 18/130,980 2023/0399410, filed Apr. 5, 2023 Dec. 14, 2023, Jennifer Sloane Lazar, Compositions and Methods for Treating Polymyalgia Rheumatica by Administering an IL-6R Antagonist.

U.S. Appl. No. 16/858,301 2020/0405851, filed Apr. 24, 2020 Dec. 31, 2020, Anita Boyapati, Method of Diagnosis and Treatment of Rheumatoid Arthritis.

U.S. Appl. No. 16/891,984 2020/0399380, filed Jun. 3, 2020 Dec. 24, 2020, Susan Boklage, Compositions and Methods for Treating Pain in Subjects With Rheumatoid Arthritis.

U.S. Appl. No. 17/615,732 2022/0242959, filed Jun. 11, 2020 Aug. 4, 2022, Chieh-I Chen, Modified Dosage of Subcutaneous Tocilizumab for Rheumatoid Arthritis.

U.S. Appl. No. 17/926,018 2023/0174657, filed May 25, 2021 Jun. 8, 2023, Inka Albrecht, Compositions Comprising an Antibody Against Interleukin-6 Receptor for the Treatment of Rheumatoid Arthritis and Methods of Using Same.

U.S. Appl. No. 17/926,123 2023/0193871, filed May 27, 2021 Jun. 22, 2023, Kerri Ford, Compositions and Methods for Treating Noninflammatory Pain in Subjects With Rheumatoid Arthritis.

Adlan, et al., Autonomic Function and Rheumatoid Arthritis—A Systematic Review, Seminars in Arthritis and Rheumatism, vol. 44, No. 3, pp. 283-304, 2014.

Angal, et al., A Single Amino Acid Substitution Abolishes the Heterogeneity of Chimeric Mouse/Human (IgG4) Antibody, Molecular Immunology, vol. 30, No. 1, pp. 105-108, Jan. 1993.

Biswas, et al., Prevalence, Types, Clinical Associations, and Determinants of Peripheral Neuropathy in Rheumatoid Patients, Annals of Indian Academy of Neurology, vol. 14, No. 3, pp. 194-197, 2011.

Boyden, et al., Non-inflamatory Causes of Pain in Patients with Rheumatoid Arthritis, Current Rheumatology Reports, vol. 18, No. 6, pp. 1-8, Apr. 20, 2016.

Brenn, et al., Sensitization of Unmyelinated Sensory Fibers of the Joint Nerve to Mechanical Stimuli by Interleukin-6 in the Rat: an Inflammatory Mechanism of Joint Pain, Arthritis & Rheumatology, vol. 56, No. 1, pp. 351-359, Jan. 2007.

Burmester, et al., Efficacy and Safety of Sarilumab Monotherapy Versus Adalimumab Monotherapy for The Treatment of Patients With Active Rheumatoid Arthritis (Monarch): A Randomised, Double-Blind, Parallel-Group Phase III Trial, Annals of the Rheumatic Diseases, vol. 76, No. 5, pp. 840-847, May 1, 2017.

Cazzola et al., Physiopathology of Pain in Rheumatology, Reumatismo, vol. 66, No. 1, pp. 4-13, 2014.

Challa, et al., Patient-provider Discordance Between Global Assessments of Disease Activity in Rheumatoid Arthritis: a Comprehensive Clinical Evaluation, Arthritis Research & Therapy, vol. 19, No. 212, pp. 1-14, 2017.

Choy, et al., Neuroendocrine and Neurophysiological Effects of Interleukin 6 in Rheumatoid Arthritis, Rheumatology, vol. 57, pp. 1885-1895, Nov. 2018.

De Haas, et al., Rheumatoid Arthritis, Typus Robustus, Annals of the Rheumatic Diseases, vol. 32, No. 1, pp. 91-92, 1973.

Deane, et al., Preclinical Rheumatoid Arthritis: Identification, Evaluation, and Future Directions for Investigation, Rheumatic Disease Clinics of North America, vol. 36, No. 2, pp. 213-241, 2010.

Durán, et al., The Effect on Treatment Response of Fibromyalgic Symptoms in Early Rheumatoid Arthritis Patients: Results From the Espoir Cohort, Rheumatology, vol. 54, No. 12, pp. 2166-2170, 2015.

Europeans Medicines Agency, Assessment Report—Kevzara, EMA/292840/2017, Committee for Medicinal Products for Human Use (CHMP), Apr. 27, 2017, Retrieved from: <<www_dot_ema_dot_europa_dot_eu/documents/assessment_report/kevzara_epar_public_assessment_report_en_dot_pdf>>.

Flodin, et al., Intrinsic Brain Connectivity in Chronic Pain: A Resting-State fMRI Study in Patients with Rheumatoid Arthritis, Frontiers in Human Neuroscience, vol. 10, No. 107, pp. 1-8, Mar. 2016.

Hammer, et al., Major Reduction of Ultrasound Detected Synovitis during Subcutaneous Tocilizumab Treatment; Results from a Multicenter 24 Weeks Study of Patients with Rheumatoid Arthritis, Arthritis & Rheumatology, vol. 70, No. S9, pp. 1537-1538, 2018.

International Search Report and Written Opinion for PCT International Patent Application No. PCT/IB2021/054652, dated Aug. 30, 2021.

Khan, et al., Determinants of Discordance in Patients' and Physicians' Rating of Rheumatoid Arthritis Disease Activity, Arthritis Care & Research (Hoboken), vol. 64, No. 2, pp. 206-214, 2012.

Kristensen, et al., Is Swollen to Tender Joint Count Ratio a New and Useful Clinical Marker for Biologic Drug Response in Rheumatoid Arthritis? Results From a Swedish Cohort, Arthritis Care & Research (Hoboken), vol. 66, No. 2, pp. 173-179, 2014.

Langer, Robert, New Methods of Drug Delivery, Science, vol. 294, No. 4976, pp. 1527-1533, 1990.

Lee, et al., Pain Persists in DAS28 Rheumatoid Arthritis Remission but Not in ACR/EULAR Remission: a Longitudinal Observational Study, Arthritis Research & Therapy, vol. 13, No. R83, pp. 1-9, 2011.

(56) References Cited

OTHER PUBLICATIONS

Maini, et al., Infliximab (Chimeric Anti-Tumour Necrosis Factor A Monoclonal Antibody) Versus Placebo in Rheumatoid Arthritis Patients Receiving Concomitant Methotrexate: a Randomised Phase III Trial, The Lancet, vol. 354, No. 9194, pp. 1932-1939, 1999.
Mcwilliams, et al., Pain Mechanisms in Rheumatoid Arthritis, Clinical and Experimental Rheumatology, vol. 35, No. 5, pp. S94-S101, 2017.
Meehan, A Microinfusor Device for the Delivery of Therapeutic Levels of Peptides and Macromolecules, Journal of Controlled Release, vol. 46, No. 1-2, pp. 107-116, 1997.
Millar, et al., Inflammatory mechanisms in tendinopathy—towards translation, Nature Reviews Rheumatology, vol. 13, No. 2, pp. 110-122, 2017.
Pincus, et al., Limitations of a Quantitative Swollen and Tender Joint Count to Assess and Monitor Patients with Rheumatoid Arthritis, Bulletin of the NYU Hospital for Joint Diseases, vol. 66, No. 3, pp. 216-223, 2008.
Pollard, et al., Fibromyalgic Rheumatoid Arthritis and Disease Assessment, Rheumatology, vol. 49, No. 5, pp. 924-928, Jan. 25, 2010.
Powell, et al., Compendium of Excipients for Parenteral Formulations, PDA Journal of Pharmaceutical Science and Technology, vol. 52, No. 5, pp. 238-311, 1998.
Rose-John, et al., Interleukin-6 Biology is Coordinated by Membrane-bound and Soluble Receptors: Role in Inflammation and Cancer, Journal of Leukocyte Biology, vol. 80, No. 2, pp. 227-236, Aug. 2006.
Sarzi-Puttini, et al., Correlation of the Score for Subjective Pain With Physical Disability, Clinical and Radiographic Scores in Recent Onset Rheumatoid Arthritis, BMC Musculoskeletal Disorders, vol. 3, No. 18, pp. 1-4, Jul. 19, 2002.
Schaible, Nociceptive Neurons Detect Cytokines in Arthritis, Arthritis Research & Therapy, vol. 16, No. 470, pp. 1-9, 2014.
Strand, et al., Sarilumab Improves Patient-reported Outcomes in Rheumatoid Arthritis Patients With Inadequate Response/Intolerance to Tumour Necrosis Factor Inhibitors, RMD Open, vol. 3, e000416, 2017.
Strand, et al., Sarilumab Plus Methotrexate Improves Patient-reported Outcomes in Patients With Active Rheumatoid Arthritis and Inadequate Responses to Methotrexate: Results of a Phase III Trial, Arthritis Research & Therapy, vol. 18, No. 198, pp. 1-10, 2016.
Studenic, et al., Discrepancies Between Patients and Physicians in Their Perceptions of Rheumatoid Arthritis Disease Activity, Arthritis & Rheumatology, vol. 64, No. 9, pp. 2814-2823, 2012.
Taylor, et al., A Transgenic Mouse That Expresses a Diversity of Human Sequence Heavy and Light Chain Immunoglobulins, Nucleic Acids Research, vol. 20, No. 23, pp. 6287-6295, Dec. 11, 1992.
Taylor, et al., Patient Perceptions Concerning Pain Management in the Treatment of Rheumatoid Arthritis, The Journal of International Medical Research, vol. 38, No. 4, pp. 1213-1224, 2010.
Walsh, et al., Mechanisms, Impact and Management of Pain in Rheumatoid Arthritis, Nature Reviews Rheumatology, vol. 10, No. 10, pp. 581-592, 2014.
Wu, et al., Receptor-Mediated in Vitro Gene Transformation by a Soluble Dna Carrier System, Journal of Biological Chemistry, vol. 262, No. 10, pp. 4429-4432, 1987.
Yang, et al., Chronic Pain: Structural and Functional Changes in Brain Structures and Associated Negative Affective States, International Journal of Molecular Sciences, vol. 20, No. 13, p. 3130, Jun. 26, 2019.
Zhou, et al., Interleukin-6: An Emerging Regulator of Pathological Pain, Journal of Neuroinflammation, vol. 13, No. 141, pp. 1-9, 2016.
U.S. Appl. No. 13/043,617, filed Oct. 25, 2011, Stevens et al.
"Highlights of Prescribing Information" for Kevzara (sarilumab), Reference ID: 4101405—Accessdata.fda.gov, May 2017.
Actemra Prescribing Information Genentech. Actemra (tocilizumab): Full Prescribing Information. 2017 Retrieved from: <<https://www.accessdata.fda.gov/drugsatfda_docs/label/2017/125276s114lbl.pdf>>.
Adan, et al., "Tocilizumab Treatment for Refractory Uveitis-Related Cystoid Macular Edema", Graefe's Archive for Clinical and Experimental Ophthalmology, vol. 251, No. 11, pp. 2627-2632, Jul. 27, 2013.
Advisory Action received for U.S. Appl. No. 13/648,521, mailed on Jul. 19, 2016, 3 Pages.
Alekseeva, "Juvenile Idiopathic Arthritis: Clinical Picture, Diagnosis, Treatment," Current Pediatrics, 2015, 14(1): 78-94, Etiology and Pathogenesis, p. 78; Treatment of Polyarticular (RF−, RF+) JIA, p. 84; and Treatment, p. 92, English Abstract included.
Aletaha et al. (2010) "Rheumatoid Arthritis Classification Criteria, ACR classification," Arthritis & Rheumatism. 62 p. 2569-2581.
Amit et al., "Three-Dimensional Structure of an Antigen-Antibody Complex at 2.8 a Resolution" Science (Aug. 1986) 233:747-753.
An et al. (2010) "The addition of tocilizumab to DMARD therapy for rheumatoid arthritis: a meta-analysis of randomized controlled trials," 66(1):49-59.
Andersson M. et al., "SAT0116 Prevalence of unacceptable pain in patients with long-standing RA", Annals of the Rheumatic Diseases, 2017, 76: p. 812-813.
Arevalo, "Tocilizumab Shows Promise for Refractory Uveitis-Related Macular Edema", URL:https://www.aao.org/editors-choice/tocilizumab-shows-promise-refractory-uveitISRWOelate, Nov. 25, 2014.
Atzeni et al., "Il-6 Involvement in pain, fatigue and mood disorders in rheumatoid arthritis and the effects of Il-6 inhibitor sarilumab", Pharmacological Research, 2019, 149: 1-8.
Barry, et al., "Pharmacotherapy for Uveitis: Current Management and Emerging Therapy", Clinical Ophthalmology, vol. 8, pp. 1891-1911, Sep. 1, 2014.
Boyapati, et al., "Sarilumab Plus Methotrexate Suppresses Circulating Biomarkers of Bone Resorption and Synovial Damage in Patients with Rheumatoid Arthritis and Inadequate Response to Methotrexate: A Biomarker Study of Mobility", Arthritis Research & Therapy, vol. 18, Article No. 225, pp. 1-12, Dec. 1, 2016.
Bresnick, "Diabetic Macular Edema—A Review", Ophthalmology, vol. 93, No. 7, pp. 989-997, Jul. 1986.
Burmester et al. (Jul. 31, 2013) "A randomised, double-blind, parallel-group study of the safety and efficacy of subcutaneous tocilizumab versus intravenous tocilizumab in combination with traditional disease-modifying antirheumatic drugs in patients with moderate to severe rheumatoid arthritis (SUMMACTA study) ," Ann. Rheum. Dis. 73:69-74.
Burmester et al., "Rheumatoid Arthritis—Sarilumab more effective than adalimumab", Nature Reviews, Rheumatology, Research Highlights, Published online Dec. 8, 2016.
Burmester et al., "Safety and efficacy of switching from adalimumab to sarilumab in patients with rheumatoid arthritis in the ongoing Monarch open-label extention", RMD Open, Rheumatic and Musculoskeletal Diseases, 2019, 5: e001017.
Burmester, et al. Unique Changes in Hemoglobin with Sarilumab Versus Adalimumab are Independent of Better Disease Control in Patients with Rheumatoid Arthritis (RA) Arthritis & Rheumatology, 2018 vol. 70, Supplement 10, Abstract 1528.
Bykerk et al., "Impact of Sarilumab on Unacceptable Pain and Inflammation Control in Moderately-to-Severely Active Rheumatoid Arthritis (RA) Patients in 3 Phase 3 Studies", Arthritis & Rheumatology (Hoboken), Oct. 1, 2019, 71(S10): Abstract No. 1393.
Bykerk et al., "Impact of sarilumab on unacceptable pain and inflammation control in moderately-to-severely active rheumatoid arthritis (RA) patients in 3 Phase 3 studies", Rheumatology, Apr. 20, 2020, 59(2): EP25.
Bykerk et al., "Impact of Sarilumab on Unacceptable Pain and Inflammation Control in Moderately-to-Severely Active Rheumatoid Arthritis Patients in 3 Phase 3 Studies", Sep. 11, 2020, retrieved from url: https://pheedloop.s3.amazonaws.com/media/events/EVEVLUEFMPIXU/files/822199_Bykerk-Vivian-RA-Unacceptable%20Pain.pdf.

(56) References Cited

OTHER PUBLICATIONS

Calabrese, et al., "IL-6 Biology: Implications for Clinical Targeting in Rheumatic Disease", Nature Reviews Rheumatology, vol. 10, No. 12, pp. 720-727, Dec. 2014.

Cao, et al., "Pharmacological Blockade of Interleukin 6 Receptor (IL-6R) Inhibits the Development of Ocular Inflammation in the Murine Model of Experimental Autoimmune Uveitis (EAU)", Investigative Ophthalmology & Visual Science, vol. 54, Issued 15, p. 5193, Jun. 2013.

Center for Drug Evaluation and Research, Application No. 761037 (Year: 2016).

Chester (Jul. 24, 2017) E-mail: "<External> CAS Registry No. RN1189541-98-7".

Cheung, et al., "2-093 Comparative Effectiveness of Biologic Dmards and Jak Inhibitors in Patients With an Inadequate Response to TNF Inhibitors: a Network Meta-analysis", International Journal of Rheumatic Diseases, Retrieved From url: <<https://onlinelibrary.wiley.com/doi/10.1111/1756-185X.13545>>.

Chichasova (2010) "fletieume peama-rompuoro apTpwTa: Taiamyeume Bonpocbi B npaimike krimumumc-ra [Treatment pf rheumatoid arthritis: tactical issues in the practice of the clinician]," fleyaupin Bpati [The Attending Physician]. No. 7/10.—English machine translation only.

Choy et al., "Indirect Treatment Comparison of the Efficacy and Safety of Sarilumab Monotherapy in Rheumatoid Arthritis Patients with Inadequate Response to Conventional Disease-Modifying Antirheumatic Drugs", Mar. 12, 2019, 36(4): 817-827.

Choy et al., "Therapeutic benefit of blocking interleukin-6 activity with an anti-interleukin-6 receptor monoclonal antibody in rheumatoid arthritis: A randomized, double-blind, placebo-controlled, dose-escalation trial", Arthritis & Rheumatology, Dec. 2002, 46(12): 3143-3150.

Choy, "Understanding the Dynamics: Pathways Involved in the Pathogenesis of Rheumatoid Arthritis", Rheumatology, vol. 51, Supplement 5, pp. v3-v11, Jul. 1, 2012.

Choy, et al., "Cardiovascular Risk in Rheumatoid Arthritis: Recent Advances in the Understanding of the Pivotal Role of Inflammation", Risk Predictors and the Impact of Treatment Rheumatology, vol. 53, pp. 2143-2154, Dec. 1, 2014.

ClinicalTrials.gov (Oct. 22, 2019) "Efficacy and Safety of GSK3196165 (Otilimab) Versus Placebo and Sarilumab in Participants With Moderately to Severely Active Rheumatoid Arthritis Who Have an Inadequate Response to Biological Disease-modifying Antirheumatic Drug (DMARDs) and/or Janus Kinase (JAK) Inhibitors (contRAst 3)", ClinicalTrials.gov Identifier: NCT04134728.

ClinicalTrials.gov, (Apr. 13, 2015) "Phase II Study to Analyze Sarilumab in Non-Infectious Uveitis", ClinicalTrials.gov Identifier: NCT01900431.

ClinicalTrials.gov, (Dec. 13, 2016) "A Repeated Dose-finding Study of Sarilumab in Children and Adolescents With Systemic Juvenile Idiopathic Arthritis (SKYPS)", ClinicalTrials.gov Identifier: NCT02991469.

ClinicalTrials.gov, (Feb. 26, 2015) "A Study Assessing the Safety and Efficacy of Sarilumab Added to Non-MTX DMARDs or as Monotherapy in Japanese Patients With Active Rheumatoid Arthritis", ClinicalTrials.gov Identifier: NCT02373202.

ClinicalTrials.gov, (Jan. 7, 2015) "Efficacy and Safety of Sarilumab and Adalimumab Monotherapy in Patients With Rheumatoid Arthritis (SARIL-RA-Monarch)", ClinicalTrials.gov Identifier: NCT02332590.

ClinicalTrials.gov, (May 18, 2016) "An Open-label, Ascending, Repeated Dose-finding Study of Sarilumab in Children and Adolescents With Polyarticular-course Juvenile Idiopathic Arthritis (pcJIA) (SKYPP)", ClinicalTrials.gov Identifier: NCT02776735.

ClinicalTrials.gov, (Oct. 7, 2010), "Evaluation of Sarilumab (SAR153191/REGN88) on Top of Methotrexate in Rheumatoid Arthritis Patients (RA-Moblility)", ClinicalTrials.gov Identifier: NCT01061736.

ClinicalTrials.gov, (Oct. 18, 2012.) "To Evaluate the Effect of SAR153191 (REGN88) Added to Other RA Drugs in Patients With RA Who Are Not Responding to or Intolerant of Anti-TNF Therapy (SARIL-RA-Target)", ClinicalTrials.gov Identifier: NCT01709578.

ClinicalTrials.gov, (Oct. 29, 2012) "Study of the Safety, Tolerability, and Bioactivity of Tocilizumab on Patients with Non-infectious Uveitis, The Stop-Uveitis Study", ClinicalTrials.gov Identifier: NCT01717170.

ClinicalTrials.gov. (Feb. 2, 2010) "Evaluation of SAR153191(REGN88) (Sarilumab) on Top of Methotrexate in Rheumatoid Arthritis Patients (RA-Mobility)," ClinicalTrials.gov. Identifier: NCT01061736.

ClinicalTrials.gov. (Nov. 7, 2013) "Evaluation of SAR153191(REGN88) (Sarilumab) on Top of Methotrexate in Rheumatoid Arthritis Patients (RA-Mobility)," ClinicalTrials.gov Identifier: NCT01061736.

ClinicalTrials.gov. (Oct. 7, 2010) "Effect of SAR153191 (REGN88) With Methotrexate in Patients With Active Rheumatoid Arthritis Who Failed INF-a Blockers," ClinicalTrials.gov Identifier: NCT01217814.

ClinicalTrials.gov. (Sep. 27, 2011) "Effect of SAR153191 (REGN88) With Methotrexate in Patients With Active Rheumatoid Arthritis Who Failed INF-a Blockers," ClinicalTrials.gov Identifier: NCT01217814.

Corevitas, Rheumatoid Arthritis Registry, Available from: https://www.corevitas.com/registry/rheumatoid-arthritis, Accessed on Aug. 26, 2022.

Cronstein, "Low-Dose Methotrexate: A Mainstay in the Treatment of Rheumatoid Arthritis", Pharmacological Reviews, Jun. 2005, 57(2): 163-172.

Curtis et al., "Determining the minimally important difference in the clinical disease activity index for improvement and worsening in early rheumatoid arthritis patients", Arthritis Care Res (Hoboken), 2015, 67(10): 1345-1353.

Curtis, et al. Reanalysis of the Multi-Biomarker Disease Activity Score for Assessing Disease Activity in the Abatacept Versus Adalimumab Comparison in Biologic-Naive Rheumatoid Arthritis Subjects with Background Methotrexate Study: Comment on the Article by Fleischmann, Arthritis & Rheumatology, Apr. 2017, vol. 69, No. 4, pp. 863-872.

Dasgupta et al., "Sarilumab in Patients With Relapsing Polymyalgia Rheumatica: A Phase 3, Multicenter, Randomized, Double Blind, Placebo Controlled Trial (Saphyr)", Annals of the Rheumatic Diseases, EULAR European Congress of Rheumatology (EULAR); Copenhagen, Denmark; Jun. 1-4, 2022, British Medical Association, GB, May 31, 2022, 81(Suppl. 1): 210-211.

Daugherty et al., "Formulation and delivery issues for monoclonal antibody therapeutics," Adv. Drug Delivery Reviews, 58:686-706, (2006).

Davis, et al., "Scale for Photographic Grading of Vitreous Haze in Uveitis", American Journal of Ophthalmology, vol. 150, No. 5, pp. 637-641, Nov. 2010.

De Benedetti et al., "FRI0549—Sarilumab, a Human Monoclonal Antibody to the Interleukin-6 (IL-6) Receptor, In Polyarticular-Course Juvenile Idiopathic Arthritis (pcJIA): A 12-Week Multinational Open-Label Dose-Finding Study", Annals of the Rheumatic Diseases, Jun. 2019, 78(Suppl 2): 969-970.

De Benedetti et al., "Sarilumab, a Human Monoclonal Antibody to the Interleukin-6 Receptor, in Polyarticular-course Juvenile Idiopathic Arthritis: A 12-week, Multinational, Open-label, Dose-Finding Study", Meeting: 2019 ACR/ARP Annual Meeting, American College of Rheumatology, Abstract No. 2710, Nov. 12, 2019.

Dennis JR., et al., "Synovial Phenotypes in Rheumatoid Arthritis Correlate with Response to Biologic Therapeutics", Arthritis Research & Therapy, vol. 16, Article No. R90, pp. 1-18, Apr. 2014.

Dhillon, Intravenous Tocilizumab: A Review of Its Use in Adults with Rheumatoid Arthritis, BioDrugs, vol. 28, pp. 75-106, 2014.

Durrani, et al., "Degree, Duration, And Causes of Visual Loss in Uveitis", British Journal of Ophthalmology, vol. 88, No. 9, pp. 1159-1162, Sep. 2004.

Eberhard A., et al., "AB0285 Predictors of unacceptalbe pain and unacceptable pain with low inflammation, in early rheumatoid arthritis", Annals of the Rheumatic Diseases, pp. 1600, 2019.

Elixhauser, et al., Comorbidity Measures for Use with Administrative Data, Medical Care, vol. 36, No. 1, pp. 8-27, Jan. 1988.

Emery et al. (2008) "IL-6 receptor inhibition with tocilizumab improves treatment outcomes in patients with rheumatoid arthritis

(56) References Cited

OTHER PUBLICATIONS refractory to anti-tumor necrosis factor biologicals: results from a 24-week multicenter randomised placebo-controlled trial," Ann. Rheum. Dis. 67:1516-1523.
Extended European Search Report received for European Patent Application No. 20167644.2, mailed on Oct. 21, 2020, 8 Pages.
Feist, et al., "Abstract 0832 Prosara—A Prospective, Multicenter, Noninterventional Study to Evaluate the Safety and Effectiveness of Sarilumab for the Treatment of Active Rheumatoid Arthritis in Regular Care in Germany", ACR Convergence, Nov. 5-9, 2020, Meeting Abstracts.
Feist, et al., "THU0165 Prosara—a Prospective, Multicenter, Non-interventional Study to Evaluate the Safety and Effectiveness of Sarilumab for the Treatment of Active Rheumatoid Arthritis in Regular Care in Germany", Annals of the Rheumaic Diseases, Scientific Abstracts, Jun. 2020.
Final Office Action received for U.S. Appl. No. 13/648,521, mailed on Feb. 11, 2016, 13 Pages.
Final Office Action received for U.S. Appl. No. 13/648,521, mailed on Mar. 10, 2014, 9 Pages.
Fleischmann et al. "Comparable Efficacy with Sarilumab Plus Methotrexate in Biologic-Experienced and Biologic-Naive Patients with Moderate-to-Severe Rheumatoid Arthritis from a Phase 3, Randomized, Double-Blind, Placebo-Controlled, International Study." Arthritis & Rheumatology. vol. 66. 111 River ST, Hoboken 07030-5774, NJ USA: Wiley-Blackwell, 2014.
Fleischmann et al., "Efficacy and Safety of Sarilumab in Connection with CsDMARDs in Patients with Active Rheumatoid Arthritis Who Were Inadequate Responders or Intolerant of Anti-TNF-alpha Therapy: Results from a Phase 3 Study", ACR Abstract 970; Nov. 8, 2015.
Fleischmann, et al., "Estimating Disease Activity using Multi-Biomarker Disease Activity Scores in Rheumatoid Arthritis Patients Treated with Abatacept or Adalimumab", Arthritis & Rheumatology, vol. 68, No. 9, pp. 2083-2089, Sep. 2016.
Fleischmann, et al., "Sarilumab and Nonbiologic Disease-Modifying Antirheumatic Drugs in Patients with Active Rheumatoid Arthritis and Inadequate Response or Intolerance to Tumor Necrosis Factor Inhibitors", Arthritis & Rheumatology, vol. 69, No. 2, pp. 277-290, Feb. 2017.
Fortin, et al., "Glossary of Selected Terms—A Systematic Review of Intravitreal Bevacizumab for the Treatment of Diabetic Macular Edema" NCBI Bookshelf, XP055753991, Retrieved from: <<https://www.ncbi.nlm.nih.gov/books/NBK169468/>>, 2 Pages, May 1, 2012.
Fragiadaki et al., Sleep Disturbances and Interleukin 6 Receptor Inhibition in Rheumatoid Arthritis, J Rheumatol., 2012, 39: 60-62.
Fransen et al., "The Disease Activity Score and the EULAR response criteria", Clinical and Experimental Rheumatology, Aug. 31, 2005, 23(5 Suppl 39): S93-99).
Gabay et al., "Tocilizumab monotherapy versus adalimumab monotherapy for treatment of rheumatoid arthritis (ADACTA): a randomised, double-blind, controlled phase 4 trial", Lancet, 2013, 381(9877): 1541-1550.
Gabay, et al., "Comparison of Lipid and Lipid-Associated Cardiovascular Risk Marker Changes After Treatment With Tocilizumab or Adalimumab in Patients with Rheumatoid Arthritis", Annals of the Rheumatic Diseases, vol. 75, pp. 1806-1812, Oct. 1, 2016.
Gabay, et al., "Effect of Sarilumab on Circulating Biomarkers of Bone and Joint Destruction in Patients with Rheumatoid Arthritis with Inadequate Response to Methotrexate", Arthritis & Rheumatology, vol. 68, Supplement 10, p. 3091, Oct. 2016.
Gabay, et al., "Identification of Sarilumab Pharmacodynamic and Predictive Markers in Patients with Inadequate Response to TNF Inhibition: A Biomarker Substudy of the Phase 3 Target Study", Rheumatic & Musculoskeletal Diseases Open, vol. 4, e000607, pp. 1-11, Mar. 1, 2018.
Gandek et al. (2004) "Psychometric evaluation of the SF-36 health survey in Medicare managed care," Health Care Financ Rev. 25(4):5-25.
Garces, et al., Comparison of Dose Escalation and Costs of Dose Escalation Between Patients With Rheumatoid Arthritis Initiating Biologic Treatment With Etanercept, Adalimumab, or Infliximab, Value in Health, vol. 19, No. 3, pp. A229-A230, 2016.
Gavrilă, et al., "Biomarkers in Rheumatoid Arthritis, What Is New?", Journal of Medicine and Life, vol. 9, Issue 2, pp. 144-148, Apr.-Jun. 2016.
Genbank, "*H. sapiens* Serum Amyloid A Protein mRNA", Complete cds, Genbank Accession No. M81349.1, Retrieved from: <<https://www.ncbi.nlm.nih.gov/nuccore/M81349.1>>, 1 Page.
Genbank, "*Homo sapiens* C-Reactive Protein (CRP)", RefSeqGene on Chromosome 1, Genbank Accession No. NG_013007.1, Retrieved from: <<https://www.ncbi.nlm.nih.gov/nuccore/NG_013007.1>>, pp. 1-4.
Genbank, "*Homo sapiens* C-X-C Motif Chemokine Ligand 13 (CXCL13)", Transcript Variant 1, mRNA, Genbank Accession No. NM_006419.2, Retrieved from: <<https://www.ncbi.nlm.nih.gov/nuccore/NM_006419.2>>, pp. 1-4., Jul. 31, 2008.
Genbank, "*Homo sapiens* Intercellular Adhesion Molecule 1 (ICAM1)", mRNA, Genbank Accession No. NM_000201.3, Retrieved from: <<https://www.ncbi.nlm.nih.gov/nuccore/NM_000201.3>>, pp. 1-5., Nov. 23, 2018.
Genbank, *Homo sapiens* Matrix Metallopeptidase 3 (MMP3), mRNA, Genbank Accession No. NM_002422.5, Retrieved from: <<https://www.ncbi.nlm.nih.gov/nuccore/NM_002422.5>>, pp. 1-4, Nov. 22, 2018.
Genentech (2014) Actemra Subcutaneous Dosing & Administration Pocket Guide. pp. 1-40.
Genovese, et al., "293 A Phase 3 Clinical Program of Three, Randomized, Double-blind, Placebo- and Comparator-controlled Studies to Assess the Efficacy and Safety of Otilimab in RA: Study Design and Methodology", Journal of Clinical Rheumatology, Retrieved From url :<<https://journals.lww.com/jclinrheum/Fulltext/2020/04001/22nd_PANLAR_Congress_Miami,_FL,_August_12_15_2020.1.aspx>>.
Genovese, et al., "Efficacy and Safety of Sarilumab in Combination With csDMARDs or as Monotherapy in Subpopulations of Patients With Moderately to Severely Active Rheumatoid Arthritis in Three Phase III Randomized", Controlled Studies, Arthritis Research & Therapy, vol. 22, No. 1, pp. 1-17, 2020.
Genovese, et al., "Long-term Safety and Efficacy of Sarilumab Plus Methotrexate on Disease Activity, Physical Function and Radiographic Progression: 5 Years of Sarilumab Plus Methotrexate Treatment", Rheumatic & Musculoskeletal Disease, vol. 5, No. 2, pp. 1-10, 2019.
Genovese, et al., "Sarilumab Plus Methotrexate in Patients with Active Rheumatoid Arthritis and Inadequate Response to Methotrexate: Results of a Phase III Study", Arthritis & Rheumatology, vol. 67, No. 6, pp. 1424-1437, Jun. 1, 2015.
Genovese, et al., "Switching Between the JAK1-selective Inhibitor Upadacitinib and Adalimumab Following Initial Non-response: Clinical and Functional Outcomes Among Rheumatoid Arthritis Patients", Oral Presentations, Jun. 12, 2019, RA therapy—JAK inhibitors and beyond.
Genovese, et al., Interleukin-6 Receptor Inhibition With Tocilizumab Reduces Disease Activity in Rheumatoid Arthritis With Inadequate Response to Disease-modifying Antirheumatic Drugs: the Tocilizumab in Combination With Traditional Disease-modifying Antirheumatic Drug Ther, Arthritis & Rheumatism: Official Journal of the American College of Rheumatology, vol. 58, No. 10, pp. 2968-2980, Sep. 29, 2008.
Georgy, et al., A Clinical Study to Assess the Pharmacokinetics and Pharmacodynamics of Tocilizumab After a Single Dose Administration by Subcutaneous and Intra Venous Routes to Healthy Subjects, Clinical Pharmacology & Therapeutics, vol. 87, No. S1, p. S60, Feb. 15, 2010.
Gordon, et al., "pANCA Antibodies in Patients With Anterior Uveitis: Identification of a Marker Antibody Usually Associated With Ulcerative Colitis", Journal of Clinical Immunology, vol. 18, No. 4, pp. 264-271, Jul. 1998.
HAQ—Health Assessment Questionnaire, Scleroderma Study Conference, English Translation, Retrieved from URL: <<http://derma.

(56) References Cited

OTHER PUBLICATIONS w3.kanazawa-u.ac.jp/SSc/pamphret/HAQ.html >>,6 Pages (4 Pages of English Translation & 2 Pages of Official Copy), Jul. 30, 2019.
Heidari et al., "Rheumatoid Arthritis: Early Diagnosis and Outcomes", Caspian Journ Intern Med., Winter 2011, 2(1): 161-170.
Hennigan et al., "Interleukin-6 inhibitors in the treatment of rheumatoid arthritis", Therapeutic and Clinical Risk Management , 4(4), 767-775. (Year: 2008).
Hirata et al., "Characterization of IL-6 Receptor Expression by Monoclonal and Polyclonal Antibodies" J. Immunol. (1989) 143(9):2900-2906.
Huizinga, et al., "Sarilumab, A Fully Human Monoclonal Antibody Against IL-6Rα in Patients with Rheumatoid Arthritis and an Inadequate Response to Methotrexate: Efficacy and Safety Results from the Randomised SARIL-RA-Mobility Part A Trial", Annals of the Rheumatic Diseases, vol. 73, No. 9, pp. 1626-1634, Sep. 1, 2014.
Humira® (Adalimumab) Injection, for Subcutaneous Use, Highlights of Prescribing Information, United States Food and Drug Administration, Retrieved from: <<https://www.accessdata.fda.gov/drugsatfda_docs/label/2018/125057s410lbl.pdf>>, 104 Pages, Dec. 2018.
Hunter, et al., "IL-6 as a Keystone Cytokine in Health and Disease", Nature Immunology, vol. 16, No. 5, pp. 448-457, May 2015.
Imagawa et al., "Safety and efficacy of tocilizumab, an anti-IL-6-receptor monoclonal antibody, in patients with polyarticular-course juvenile idiopathic arthritis", Modern Rheumatology, Jun. 12, 2011, 22(1): 109-115.
International Nonproprietary Names for Pharmaceutical Substances (INN) WHO Drug Information, vol. 25, No. 4, 2011; 53 pages.
International Search Report and Written Opinion for PCT International Patent Application No. PCT/US2020/016203, mailed Jul. 14, 2020.
International Search report and Written Opinion for PCT International Patent Application No. PCT/US2020/035871, mailed on Sep. 28, 2020.
International Search Report and Written Opinion Received for PCT Application No. PCT/US2020/037325, mailed on Oct. 27, 2020.
International Search Report and Written Opinion received for PCT Patent Application No. PCT/IB2021/054546, mailed on Sep. 14, 2021.
International Search Report and Written Opinion received for PCT Patent Application No. PCT/US2016/060344, mailed on Mar. 13, 2017.
International Search Report and Written Opinion received for PCT Patent Application No. PCT/US2017/021149, mailed on Jul. 18, 2017.
International Search Report and Written Opinion received for PCT Patent Application No. PCT/US2020/029930, mailed on Oct. 8, 2020.
International Search Report with Written Opinion corresponding to International Patent Application No. PCT/ EP2012/070052, mailed Dec. 7, 2012.
International Search Report with Written Opinion corresponding to International Patent Application No. PCT/ US2014/066856, mailed Apr. 2, 2015.
International Search Report with Written Opinion corresponding to International Patent Application No. PCT/US2015/050291, mailed Dec. 1, 2015.
International Search Report with Written Opinion corresponding to International Patent Application No. PCT/US2023/065361, mailed Jul. 14, 2023.
Jones, et al., Comparison of Tocilizumab Monotherapy Versus Methotrexate Monotherapy in Patients With Moderate to Severe Rheumatoid Arthritis: the Ambition Study, Annals of the Rheumatic Diseases, vol. 69, No. 01, pp. 88-96, 2010.
Kaneko, Tocilizumab in Rheumatoid Arthritis: Efficacy, Safety and Its Place in Therapy, Therapeutic Advances in Chronic Disease, vol. 4, No. 1, pp. 15-21, 2013.
Karmakar, et al., "Bone Damage in Rheumatoid Arthritis—Mechanistic Insights and Approaches to Prevention", Rheumatic Diseases Clinics of North America, vol. 36, No. 2, 19 Pages, May 1, 2010.
Kawashima, et al., "Soluble IL-6 Receptor in Vitreous Fluid of Patients With Proliferative Diabetic Retinopathy", Japanese Journal of Ophthalmology, vol. 51, No. 2, pp. 100-104, Apr. 6, 2007.
Kimel et al., "Adalimumab plus methotrexate improved SF-36 scores and reduced the effect of rheumatoid arthritis (RA) on work activity for patients with early RA", The Journal of Rheumatology, Feb. 2008, 35(2): 206-215.
Kishimoto, et al., "Interleukin-6 (IL-6)", The Cytokine Handbook. Ed.: Thomson. Academic Press. London, United Kingdom, vol. 12, pp. 281-304, Jan. 1, 2003.
Kivitz (Nov. 2014) "Subcutaneous Tocilizumab vs Placebo in Combination with Disease Modifying Antirheumatic Drugs in Patients with Rheumatoid Arthritis," Arthritis Care Res. (Hoboken). 66(11):1653-1661.
Klein, et al. FRI0549—Efficacy and Safety of Tocilizumab in Systemic and Polyarticular Juvenile Idiopathic Arthritis—Data of Toe Biker Registry Squibb, Johnson & Johnson, Novartis, Pfizer, Fieckitt Benkiser, and Roche Jun. 14, 2019 pp. 969-970.
Kojima, et al., Depression, Inflammation, and Pain in Patients With Rheumatoid Arthritis, Arthritis & Rheumatism (Arthritis Care & Research), vol. 61, No. 8, pp. 1018-1024, Aug. 15, 2009.
Kremer, et al., Tocilizumab Inhibits Structural Joint Damage in Rheumatoid Arthritis Patients With Inadequate Responses to Methotrexate, Arthritis & Rheumatism vol. 63, No. 3, pp. 609-621, 2011.
Kringelbach, et al., "Identification of New Biomarkers to Promote Personalised Treatment of Patients with Inflammatory Rheumatic Disease: Protocol for an Open Cohort Study", British Medical Journal Open, vol. 8, e019325, pp. 1-8., Feb. 1, 2018.
Lamb et al., "Sarilumab: A Review in Moderate to Severe Rheumatoid Arthritis Drugs", Drugs, 2018, 78: 929-940.
Lederman et al. "A Single Amino Acid Substitution in a Common African Allele of the CD4 Molecule Ablates Binding of the Monoclonal Antibody, OKT4" Molecular Immunology (1991) 28(11):1171-1181.
Lee et al., "Disease modifying drugs in adult rheumatoid arthritis", Australian Prescriber, Apr. 2003, 26: 36-40.
Li et al. "Temporal associations between interleukin 22 and the extracellular domains of IL-22R and IL-10R2" International Immunology (2004) 4:693-708.
Lin, "Targeting Interleukin-6 for Noninfectious Uveitis, Clinical Ophthalmology", vol. 9, pp. 1697-1702, Sep. 1, 2015.
Lipsky, "Interleukin-6 and Rheumatic Diseases", Arthritis Research & Therapy, vol. 8, Suppl 2, S4, pp. 1-5, Jan. 1, 2006.
Lourdudoss et al., "Dietary intake of polyunsaturated fatty acids and pain in spite of inflammatory control among methotrexate-treated early rheumatoid arthritis patients", Arthritis Care and Research, Feb. 2018, 70(2): 205-212.
Maini, et al., Double-blind Randomized Controlled Clinical Trial of the Interleukin-6 Receptor Antagonist, Tocilizumab, in European Patients With Rheumatoid Arthritis Who Had an Incomplete Response to Methotrexate, Arthritis & Rheumatism, vol. 54, No. 9, pp. 2817-2829, Aug. 31, 2006.
Matcham, et al., Psychological Correlates of Fatigue in Rheumatoid Arthritis: A Systematic Review, Clinical Psychology Review, vol. 39, pp. 16-29, Jul. 2015.
Matcham, et al., Symptoms of Depression and Anxiety Predict Treatment Response and Long-term Physical Health Outcomes in Rheumatoid Arthritis: Secondary Analysis of a Randomized Controlled Trial, Rheumatology, vol. 55, Issue 2, pp. 268-278, Feb. 2016.
Matcham, et al., The Prevalence of Depression in Rheumatoid Arthritis: A Systematic Review and Meta-analysis, Rheumatology, vol. 52, Issue 12, pp. 2136-2148, Sep. 3, 2013.
Matteson, "Current Treatment Strategies for Rheumatoid Arthritis", Mayo Clinic Proceedings, vol. 75, pp. 69-74, Jan. 2000.
Mcgovern, (Oct. 19, 2016) "Center for Drug Evaluation and Research", Application No. 761037Orig1s000, pp. 01-278.

(56) References Cited

OTHER PUBLICATIONS

Mcinnes, et al., "Cytokines in the Pathogenesis of Rheumatoid Arthritis", Nature Reviews, Immunology, vol. 7, pp. 429-442, Jun. 2007.
Medscape, Actemra, Retrieved online: <URL: https://reference.medscape.com/drug/actennra-tocilizunnab-999419>, Retrieved on Feb. 8, 2022.
Meehan et al. (1996) "A microinfusor device for the delivery of therapeutic levels of peptides and macromolecules," Journal of Controlled Release. 46:107-116.
Merida, et al., "New Immunosuppressive Therapies in Uveitis Treatment", International Journal of Molecular Sciences, vol. 16, No. 8, pp. 18778-18795, Aug. 11, 2015.
Mesquida, et al., "Long-Term Effects of Tocilizumab Therapy for Refractory Uveitis-Related Macular Edema", Ophthalmology, vol. 121, No. 12, pp. 2380-2386, Sep. 6, 2014.
Mihara et al., 2005, Tocilizumab inhibits signal transduction mediated by both MIL-6R and sIL-6R, but not by the receptors of other members of IL-6 cyotkine family, International Immunopharmacology 5:1731-1740.
Montaño et al., "Influence of the Isotype of the Light Chain on the Properties of IgG", Journal of Immunology, 2002, 168: 224-231.
Muszbek et al., "Economic Evaluation of Sarilumab in the Treatment of Adult Patients with Moderately-to-Severely Active Rheumatoid Arthritis Who Have an Inadequate Response to Conventional Synthetic Disease-Modifying Antirheumatic Drugs", Advances in Therapy, Apr. 19, 2019, 36(6): 1337-1357.
Nadkarni, et al., Incidence of Dose Escalation and Impact on Biologic Costs Among Patients With Rheumatoid Arthritis Treated With Three Intravenous Agents, Journal of Comparative Effectiveness Research, vol. 6, No. 8, pp. 671-682, 2017.
Nasonov, E.L. et al, "Prospects of pharmacotherapy rheumatoid arthritis: monoclonal antibodies", Nauchnopraktych Rheumatol., 2012, 52(3): 75-82.
NCBI, C-Reactive Protein Isoform 1 Precursor [*Homo sapiens*], NCBI Reference Sequence: NP_001315986.1, Retrieved from: <<https://www.ncbi.nlm.nih.gov/protein/NP_001315986.1>>, pp. 1-3, Jun. 29, 2016.
NCBI, C-X-C Motif Chemokine 13 Precursor [*Homo sapiens*], NCBI Reference Sequence: NP_006410.1, Retrieved from: <<https://www.ncbi.nlm.nih.gov/protein/NP_006410.1>>, pp. 1-3.
NCBI, Intercellular Adhesion Molecule 1 Precursor [*Homo sapiens*], NCBI Reference Sequence: NP_000192.2, Retrieved from: <<https://www.ncbi.nlm.nih.gov/protein/NP_000192.2>>, pp. 1-4, Feb. 8, 2008.
NCBI, Matrix Metallopeptidase 3 (Stromelysin 1, Progelatinase) [*Homo sapiens*], NCBI Reference Sequence: EAW67032.1, Retrieved from: <<https://www.ncbi.nlm.nih.gov/protein/EAW67032.1>>, pp. 1-2, Mar. 23, 2015.
NCBI, PubChem SID: 135626879, National Library of Medicine, Apr. 5, 2012, Retrieved from: <<https://pubchem.ncbi.nlm.nih.gov/substance/135626879>>.
NCBI, Serum Amyloid A [*Homo sapiens*], NCBI Reference Sequence: AAB24060.1, Retrieved from: <<https://www.ncbi.nlm.nih.gov/protein/AAB24060.1>>, 1 Page, Jul. 28, 2016.
New Drug Approvals Retrieved from: <<https://www.drugs.com/newdrugs.html>> pp. 1-7, 2019.
Nguyen et al., "The Saturn Study (SARIL-NIU): Sarilumab for the Treatment of Posterior Segment Non-Infectious Uveitis (NIU)", Investigative Ophthalmology & Visual Science, vol. 56, No. 7, 3116, Jun. 2015.
Nicassio, et al. (Jan. 2012) "The Contribution of Pain and Depression to Self-Reported Sleep Disturbance in Patients with Rheumatoid Arthritis", Pain, vol. 153, No. 1, pp. 107-112.
Nieminen, et al., "The Use of the ATF System to Culture Chinese Hamster Ovary Cells in a Concentrated Fed-Batch System", BioPharm International, vol. 24, Issue 6, pp. 1-8, Jun. 1, 2011.
Nihon Naika Gakkai Zasshi, Japan Internal Medical Association Magazine, vol. 101, No. 10, pp. 2893-2898.
Nishimoto et al. (2009) "Study of active controlled tocilizumab monotherapy for rheumatoid arthritis patients with an inadequate response to methotrexate (SATORI): significant reduction in disease activity and serum vascular endothelial growth factor by IL-6 receptor inhibition therapy," Modem Rheumatology. 19(1):12-19.
Nishimoto, et al., Humanized Antihuman IL-6 Receptor Antibody, Tocilizumab, Part of the Handbook of Experimental Pharmacology, vol. 181, Therapeutic Antibodies, pp. 151-160, 2008.
Non-Final Office Action received for U.S. Appl. No. 13/648,521, mailed on Jul. 3, 2014.
Non-Final Office Action received for U.S. Appl. No. 13/648,521, mailed on Jun. 26, 2015.
Non-Final Office Action received for U.S. Appl. No. 13/648,521, mailed on Mar. 19, 2015.
Non-Final Office Action received for U.S. Appl. No. 13/648,521, mailed on Oct. 18, 2013.
Non-Final Office Action received for U.S. Appl. No. 14/350,973, mailed on Feb. 5, 2016.
Non-Final Office Action received for U.S. Appl. No. 14/350,973, mailed on Oct. 18, 2019.
Notice of Allowance received for U.S. Appl. No. 14/350,973, mailed on Jun. 14, 2016.
Nussenblatt, et al., "Standardization of Vitreal Inflammatory Activity in Intermediate and Posterior Uveitis", Ophthalmology, vol. 92, No. 4, pp. 467-471, Apr. 1, 1985.
Ogata, et al., Long-term Safety and Efficacy of Weekly Subcutaneous Tocilizumab Monotherapy in Patients With Rheumatoid Arthritis Who Had an Inadequate Response to Subcutaneous Tocilizumab Every Other Week: Results From the Open-label Extension of the Shinobi Study, Modern Rheumatology, vol. 29, Issue 5, pp. 767-774, Sep. 3, 2019.
Ogata, et al., Subcutaneous Tocilizumab: Recent Advances for the Treatment of Rheumatoid Arthritis, Expert Opinion on Drug Delivery, vol. 16, Issue 6, pp. 639-648, Jun. 3, 2019.
Ohta, et al., Optimal Dose Prediction by Pharmacokinetic and Biomarker Response of Subcutaneous Tocilizumab Treatment A Phase I/II Study Evaluating the Safety, Pharmacokinetics and Clinical Response in Patients with Rheumatoid Arthritis, Arthritis & Rheumatism, vol. 62, Supplement 10, pp. 1-2, Oct. 1, 2010.
Ongkosuwito, et al., "Analysis of Immunoregulatory Cytokines in Ocular Fluid Samples From Patients With Uveitis", Investigative Ophthalmology & Visual Science, vol. 39, No. 13, pp. 2659-2665, Dec. 1, 1998.
Overman, et al., The Prospective Association Between Psychological Distress and Disease Activity in Rheumatoid Arthritis: a Multilevel Regression Analysis, Annals of the Rheumatic Diseases, vol. 71, No. 2, pp. 192-197, 2012.
Panka et al., "Variable Region Framework Differences Result in Decreased or Increased Affinity of Variant Anti-Digoxin Antibodies" Proc. Natl. Acad. Sci. USA (May 1988) 85:3080-3084.
Pappas, et al., Dosing of Intravenous Tocilizumab in a Real-World Setting of Rheumatoid Arthritis: Analyses from the Corrona Registry, Rheumatology and Therapy, vol. 3, pp. 103-115, Feb. 8, 2016.
Patro et al., "Protein formulation and fill-finish operations," Biotechnol Annu Rev, 8:55-84, (2002). Abstract only.
Paul-Pletzer, 2006, Tocilizumab: Blockade of interleukin-6 signaling pathway as a therapeutic strategy for inflammatory disorders, Drugs of Today 42(9):559-576.
Peichl, "Biologikatherapie in der Rheumatologie", DoctorConsult—The Journal. Wissen fur Klinik und Praxis, Nov. 2011, 2(3): e164-e166.
Pelechas et al., "Clinical evaluation of the safety, efficacy and tolerability of sarilumab in the treatment of moderate to severe rheumatoid arthritis", Therapeutics and Clinical Risk Management, Sep. 1, 2019, vol. 15, pp. 1073-1079.
Perez, et al., "Elevated Levels Of Interleukin 6 in the Vitreous Fluid of Patients With Pars Planitis and Posterior Uveitis: The Massachusetts Eye & Ear Experience and Review of Previous Studies", Ocular Immunology and Inflammation, vol. 12, No. 3, pp. 193-201, Sep. 2004.
Pham et al., "Patient acceptable symptomatic state (PASS)", Joint Bone Spine, Jul. 2009, 76(4): 321-323.
Powchik (2010), Regeneron Investor Day, p. 1-19.

(56) References Cited

OTHER PUBLICATIONS

Presta, "Engineering of therapeutic antibodies to minimize immunogenicity and optimize function" Advanced Drug Delivery Reviews (2006) 58:640-656.
Pulawski et al., "Certain therapies linked to pulmonary toxicity among patients with rheumatic diseases", Healio, May 20, 2015, obtained from url: https://www.healio.com/news/rheumatology/20150520/certain-therapies-linked-to-pulmonary-toxicity-among-patients-with-rheumatic-diseases.
Radin et al. (Jan. 1, 2010) "Safety and effects on markers of inflammation of subcutaneously administered regn88/ sar153191 (regn88), an interleukin-6 receptor inhibitor, in patients with rheumatoid arthritis: findings from phase 1 studies," [Abstract] Annals of the Rheumatic Diseases. 69(Suppl. 3):99.
Radin et al. (Nov. 2010) "REGN88/SAR153191, a Fully-Human Interleukin-6 Receptor Monoclonal Antibody, Reduces, Acute Phase Reactants in Patients with Rheumatoid Arthritis: Preliminary Observations from Phase 1, Studies," [Abstract] Arthritis. Rheum. 62(Suppl. 10):1121.
Rafique, et al., "Evaluation of the Binding Kinetics and Functional Bioassay Activity of Sarilumab and Tocilizumab to the Human IL-6 Receptor (IL-6r) alpha", Annals of the Rheumatic Diseases, vol. 72, Issue Suppl 3, pp. A797.1-A797, Jun. 23, 2013.
Raimondo et al., "Profile of sarilumab and its potential in the treatment of rheumatoid arthritis", Drug Design, Development and Therapy, May 24, 2017, 11: 1593-1603.
Reddy et al., "Elimination of Fc Receptor-Dependent Effector Functions of a Modified IgG4 Monoclonal Antibody to Human CD4," Journal of Immunology, 164:1925-1933 (2000).
Redlich et al., "Inflammatory bone loss: pathogenesis and therapeutic intervention", Nat Rev Drug Discov., Mar. 2012, 11(3): 234-250.
Regeneron Pharmaceuticals (Jul. 12, 2011) "Sanofi and Regeneron Report Positive Phase 2b Trial Results with Sarilumab in Rheumatoid Arthritis," Acquire Media. Accessible on the Internet at URL: http://web.archive.org/web/20110818152737/http://investorregeneron.com/releasedetail.cfm?ReleaseID=590869. [Last Accessed May 4, 2016].
Regeneron Pharmaceuticals (Jul. 12, 2011) "Evaluation of Sarilumab (SAR153191/REGN88) on Top of Methotrexate in Rheumatoid Arthritis Patients (RA-Mobility)", Retrieved from the internet from URL: <<https://clinicaltrials.gov/ct2/results?term=SAR+153191=mobility>>.
Regeneron Pharmaceuticals, Inc. (Jun. 12, 2014) "Sanofi and Regeneron announce new, detailed data from positive Sarilumab phase 3 rheumatoid arthritis trial at EULAR," Press Release. Acquire Media.
Regeneron Pharmaceuticals, Inc. (Nov. 22, 2013) "Sanofi and Regeneron report positive results with Sarilumab in first phase 3 rheumatoid arthritis registration trial," Press Release. Acquire Media.
Regeneron Pharmaceuticals, Inc., "Sanofi and Regeneron Announce Patient Enrollment in Two Phase 3 Trials With Sarilumab in Rheumatoid Arthritis (RA)", Online Publication, May 15, 2013 at 1:00 AM EDT.
Reichert (Jan. 1, 2011) "Antibody-based therapeutics to watch in 2011," MAbs. 3:76-99.
Restriction Requirement received for U.S. Appl. No. 13/648,521, mailed on Jun. 10, 2013, 7 Pages.
Restriction Requirement received for U.S. Appl. No. 14/350,973, mailed on Aug. 19, 2015, 8 Pages.
Riancho-Zarrabeitia, et al., "Efficacy of Tocilizumab in Patients with Uveitis Refractory to Other Biologic Drugs: A Multicenter Study on 31 Cases", 2014 ACR/ARHP Annual Meeting Abstract No. 1249, Retrieved from: <<https://acrabstracts.org/abstract/efficacy-of-Tocilizumab-in-patients-with-uveitis-refractory-to-other-biologic-drugs-a-multicenter-study-on-31-cases/>>, Retrieved on Sep. 14, 2020.
Roche, Anti-Human IL-6 Receptor Monoclonal Antibody "Actemra" Subcutaneous Injection Demonstrates Efficacy in Rheumatoid Arthritis in Phase III Clinical Study, Jul. 19, 2011, Retrieved online: <URL: https://www.roche.com/dann/jcr:c49f4e4e-d60e-48cc-a14e-c0f1f4107b24/en/inv-update-2011-07-19b-annex.pdf>, Retrieved on Feb. 8, 2022.
Rudikoff et al., "Single Amino Acid Substitution Altering Antigen-Binding Specificity" Proc. Natl. Acad. Sci. USA (Mar. 1982) 79:1979-1983.
Salaffi et al. "The health-related quality of life in rheumatoid arthritis, ankylosing spondylitis, and psoriatic arthritis: a comparison with a selected sample of healthy people", Health and Quality of Life Outcomes, Biomed Central, vol. 7, No. 1, pp. 25, 2009.
Sanofi and Regeneron (May 21, 2015) "Sanofi and Regeneron announce positive topline results from phase 3 studies with sarilumab in patients with rheumatoid arthritis," Press Release. Sanofi. Accessible on the Internet at URL: http://mediaroom.sanofi.com/sanoThand-regeneron-announce-positive-topline-results-from-phase-3-studies-with-sarilumab-in-patients-with-rheumatoid-arthritis-2. [Last Accessed Aug. 30, 2016].
Sanofi and Regeneron (Nov. 8, 2015) "Regeneron and Sanofi Present Results from Pivotal Phase 3 Study of Sarilumab at American College of Rheumatology Annual Meeting," Press Release. Regeneron Pharmaceuticals, Inc. Accessible on the Internet at URL: http://investorregeneron.com/releasedetail.cfm?releaseid=941387. [Last Accessed Aug. 30, 2016].
Schett, "Physiological Effects of Modulating the Interleukin-6 Axis", Rheumatology, vol. 57, Supplement 2, pp. ii43-ii50, Feb. 1, 2018.
Schett, et al., "Bone Erosion in Rheumatoid Arthritis: Mechanisms, Diagnosis and Treatment", Nature Reviews Rheumatology, vol. 8, No. 11, 22 Pages, Nov. 2012.
Scott, "Sarilumab: First Global Approval", Drugs, 2017, 77: 705-712.
Sebba et al., "Comparative Effectiveness of TNF Inhibitor vs IL-6 Receptor Inhibitor as Monotherapy or Combination Therapy with Methotrexate in Patients with Rheumatoid Arthritis: Analysis from the CorEvitas RA Registry", Poster No. 0834, ACR Convergence—Virtual, Nov. 1-10, 2021.
Sebba, "Comparative Effectiveness of TNF Inhibitor vs IL-6 Receptor Inhibitor as Monotherapy or Combination Therapy with Methotrexate in Patients with Rheumatoid Arthritis: Analysis from the CorEvitas RA Registry", SAR-54318 TNFi/IL-6Ri Mono/Combo Audio narration, ACR Convergence—Virtual, Nov. 1-10, 2021.
Sechidis, et al., "Distinguishing Prognostic and Predictive Biomarkers: An Information Theoretic Approach", Bioinformatics, vol. 34, No. 19, pp. 3365-3376, Oct. 1, 2018.
Seth, et al., "Development of a New Bioprocess Scheme Using Frozen Seed Train Intermediates to Initiate CHO Cell Culture Manufacturing Campaigns", Biotechnology and Bioengineering, May 2013, vol. 110, Issue 5, pp. 1376-1385.
Shields et al., "Lack of Fucose on Human IgG1 N-Linked Oligosaccharide Improves Binding to Human Fc gamma RIII and Antibody-dependent Cellular Toxicity," Journal of Biological Chemistry, 277(30):26733-26740 (2002).
Singh, et al., 2015 American College of Rheumatology Guideline for the Treatment of Rheumatoid Arthritis, Arthritis & rheumatology, vol. 68, No. 1, pp. 1-26, 2016.
Smolen et al. (2008) "Effect of interleukin-6 receptor inhibition wtth tocilizumab in patients with rheumatoid arthritic (Option study): a double blind, placebo-controlled, randomised trial," Lancet. 371:987-997.
Smolen et al., "Rheumatoid arthritis", Lancet, 2016, 388(10055): 2023-2038.
Smolen, et al., "The Assessment of Disease Activity in Rheumatoid Arthritis", Clinical and Experimental Rheumatology, vol. 28, Supplement 59, pp. S18-S27, May 1, 2010.
Smolen, et al., EULAR Recommendations for the Management of Rheumatoid Arthritis With Synthetic and Biological Disease-modifying Antirheumatic Drugs: 2016 Update, Annals of the Rheumatic Diseases, vol. 76, No. 6, pp. 960-977, 2017.
Solomon, et al., "Patterns of Cardiovascular Risk in Rheumatoid Arthritis", Annals of the Rheumatic Diseases, vol. 65, pp. 1608-1612, Dec. 1, 2006.
Song, et al., "Comparative Evaluation of the Effects of Treatment With Tocilizumab and TNF-α Inhibitors on Serum Hepcidin, Ane-

(56) References Cited

OTHER PUBLICATIONS mia Response and Disease Activity in Rheumatoid Arthritis Patients", Arthritis Research & Therapy, vol. 15, Article No. R141, pp. 1-10, Oct. 1, 2013.
Spectrum Laboratories, Inc., "Hollow Fiber Filters", Datasheet [online], Spectrumlabs.com, Copyright 1995-2015, Retrieved from: <<URL: http://www.spectrumlabs.com/filtration/mPESKrosFloList.html>>, Retrieved on: Jun. 12, 2015.
Stamp et al., "The use of low dose methotrexate in rheumatoid arthritis—are we entering a new era of therapeutic drug monitoring and pharmacogenomics?", Biomedicine & Pharmacotherapy, 2006, 60: 678-687.
Steel et al., "2015 EULAR-ACR recommendations for polymyalgia rheumatica: the message and next steps", Rheumatology, Jun. 17, 2016, 55(6): 955-956, Advance Acess Publication Dec. 17, 2015.
Strand et al., "Patient-reported outcomes from a randomized phase III trial of sarilumab monotherapy versus adalimumab monotherapy in patients with rheumatoid arthritis", Arthritis Res Ther., 2018, 20(1): 129.
Strand, et al., "Health-related Quality of Life Outcomes of Adalimumab for Patients with Early Rheumatoid Arthritis: Results from a Randomized Multicenter Study", The Journal of Rheumatology, vol. 39, pp. 63-72, Jan. 1, 2012.
Study of the Safety, Tolerability, and Bioactivity of Tocilizumab on Patients With Non-infectious Uveitis, The Stop-Uveitis Study, ClinicalTrials.gov Archive, Oct. 29, 2012.
Suttorp-Schulten, et al., "Recent Developments in the Treatment of Posterior Uveitis", Ocular Immunology and Inflammation, vol. 4, No. 4, pp. 207-217, 1996.
Świerkot et al., "Methotrexate in rheumatoid arthritis", Pharmacological Reports, 2006, 58: 473-492.
Taylor, (Jun. 2010) "Pharmacology of TNF Blockade in Rheumatoid Arthritis and Other Chronic Inflammatory Diseases", Current Opinion in Pharmacology, vol. 10, Issue 3, pp. 308-315.
The Chemical Abstracts Service (CAS) entry for registration No. 1189541-98-7.
Turnier et al., "Tocilizumab for treating juvenile idiopathic arthritis", Expert Opinion on Biological Therapy, 2016, 16(4): 559-566.
Uchiyama et al., "Tocilizumab, a Humanized Anti-interleukin-6 Receptor Antibody, Ameliorates Joint Swelling in Established Monkey Collagen-Induced Arthritis" Biol. Pharm. Bull. (2008) 31(6):1159-1163.
Ueno et al., "3-145: The efficacy and safety of additional tocilizumab in patients with polymyalgia rheumatica resistant to or intolerant of conventional therapy", AU, Apr. 1, 2019, 22(S3): 204.
United States Adopted Names Council (Date Publicly Available Unclear) "Statement on a nonproprietary name adopted by the USAN council: Sarilumab," CAS Registry No. 1189541-98-7.
United States Census Bureau. Census Regions and Divisions of the United States, Retrieved from: <<https://www2.census.gov/geo/pdfs/maps-data/maps/reference/us_regdiv.pdf>>, Accessed on: Apr. 8, 2019.
Valentincic, et al., "Intraocular and Serum Cytokine Profiles in Patients With Intermediate Uveitis", Molecular Vision, vol. 17, pp. 2003-2010, Jul. 20, 2011.
Van Herwaarden, et al., Dose Reduction of Tocilizumab in Rheumatoid Arthritis Patients With Low Disease Activity, Clinical and Experimental Rheumatology, vol. 32, pp. 390-394, 2014.
Van Vollenhoven, Sex Differences in Rheumatoid Arthritis: More Than Meets the Eye, BMC Medicine, vol. 7, No. 12, pp. 1-4, Mar. 30, 2009.
Vasanthi, et al. (Dec. 2007) "Role of Tumor Necrosis Factor-Alpha in Rheumatoid Arthritis: A Review", APLAR Journal of Rheumatology, vol. 10, No. 4, pp. 270-274.
Wang et al., "Minireview: Antibody Structure, Instability, and Formulation," Journal of Pharmaceutical Sciences, 96(1):1-26, (2007).
Wang, "Instability, stabilization, and formulation of liquid protein pharmaceuticals," Int'l J. Pharmaceutics, 185(2):129-188, (1999).
Wei et al., "Serum Levels of IL-6 and TNF-α May Correlate with Activity and Severity of Rheumatoid Arthritis", Med Sci Monit., 2015, 21: 4030-4038.
Wells, et al., "Immunogenicity of Sarilumab Monotherapy in Patients with Rheumatoid Arthritis Who Were Inadequate Responders or Intolerant to Disease-Modifying Antirheumatic Drugs", Rheumatology and Therapy, vol. 6, No. 3, pp. 339-352, May 14, 2019.
Whalley et al. (1997) "Quality of life in rheumatoid arthritis," Br. J. Rheumatol. 36:884-888.
Wiens, et al., "A Systematic Review and Meta-Analysis of the Efficacy and Safety of Adalimumab for Treating Rheumatoid Arthritis", Rheumatology International, vol. 30, Issue 8, pp. 1063-1070, Jun. 1, 2010.
Wolfe et al., "Sleep Disturbance in Patients with Rheumatoid Arthritis: Evaluation by Medical Outcomes Study and Visual Analog Sleep Scales", J Rheumatol., 2006, 33:1942-1951.
Woods, et al., "Container System for Enabling Commercial Production of Cryopreserved Cell Therapy Products", Regenerative Medicine, vol. 5, No. 4, pp. 659-667, Jul. 15, 2010.
Yamamura, "FRI0266. The Real-World Efficacy of the 2015 EULAR/ACR Recommendations for the Management of Polymyalgia Rheumatica with Additional Tocilizumab Therapy", Annals of the Rheumatic Diseases, Jun. 13, 2020, 79(Suppl 1), 717.2-718.
Yokota et al., "Efficacy and safety of tocilizumab in patients with systemic-onset juvenile idiopathic arthritis: a randomised, double-blind, placebo-controlled, withdrawal phase III trial", The Lancet, Mar. 22, 2008, 371(9617): pp. 998-1006.
Yoo et al., "Exosomal amyloid A and lymphatic vessel endothelial hyaluronic acid receptor-1 proteins are associated with disease activity in rheumatoid arthritis", Arthritis Research & Therapy, 2017, 19(1): 119.
Yoshiii, I. et al, "Influence of pain score measured by a visual analog scale (PS-VAS) on the Health Assessment Questionnaire Disability Index and 28 joint-Disease Activity Index with C-reactive protei in rheumatoid arthritis patients", INT J, Rheum DID, 2018, 21: 1955-1961.
Yoshimura, et al., "Comprehensive Analysis of Inflammatory Immune Mediators in Vitreoretinal Diseases", PLoS One, vol. 4, No. 12, pp. 1-9, Jan. 1, 2009.
Avdeeva et al., "Idiopathic Fibrosing Alveolitis", RMJ, Respiratory Diseases, Feb. 17, 1998, 4: 4.
Bharucha et al., "Growth During Tocilizumab Therapy for Polyarticular-course Juvenile Idiopathic Arthritis: 2-year Data from aPhase III Clinical Trial", The Journal of Rheumatology, Jul. 1, 2018, 745(8): 1173-1179.
Boleto et al., "Safety of combination therapy with two bDMARDs in patients with rheumatoid arthritis: A systematic review and meta-analysis", Seminars in Arthritis and Rheumatism, Aug. 2019, 49(1): 35-42.
Burmester et al., "Efficacy and safety of subcutaneous tocilizumab versus intravenous tocilizumab in combination with traditional DMARDs in patients with RA at week 97 (SUMMACTA)", Annals of the Rheumatic Diseases, Jun. 8, 2015, vol. 75, No. 1, pp. 68-74.
Chambers et al., "Serum Amyloid A Protein Concentration in Rheumatoid Arthritis and Its Role in Monitoring Disease Activity", Annals of the Rheumatic Diseases, Jan. 1, 1983, 42(6): 665-667.
Choi, "Issue & Trend: Rheumatoid Arhtritis", Korea Pharmaceutical Information Center, 2000. In Korean.
Choy et al., "Subcutaneous tocilizumab in rheumatoid arthritis: findings from the common-frame work phase 4 study programme TOZURA conducted in 22 countries", Rheumatology, Mar. 1, 2018, 57(3): 499-507.
ClinicalTrials.gov (Jun. 18, 2021) "A Randomized, Double-blind, Placebo-controlled Study to Evaluate the Efficacy and Safety of Sarilumab in Patients With Polymyalgia Rheumatica", ClinicalTrials.gov ID NCT03600818.
ClinicalTrials.gov (May 21, 2020) "Efficacy and Safety of GSK3196165 (Otilimab) Versus Placebo and Sarilumab in Participants With Moderately to Severely Active Rheumatoid Arthritis Who Have an Inadequate Response to Biological Disease-modifying Antirheumatic Drug (DMARDs) and/or Janus Kinase (JAK) Inhibitors (contRAst 3)", ClinicalTrials.gov Identifier: NCT04134728.

(56) References Cited

OTHER PUBLICATIONS

ClinicalTrials.gov, "Efficacy, Safety and Tolerability of Repeated Dosis of Intravitreous Bevacizumab in Uveitic Macular Oedema", ClinicalTrials.gov ID: NCT01095809, Mar. 23, 2012.
ClinicalTrials.gov, (Jun. 8, 2015) "Phase II Study to Analyze Sarilumab in Non-Infectious Uveitis", ClinicalTrials.gov Identifier: NCT01900431.
ClinicalTrials.gov. (Jan. 17, 2017) "A Study of the Efficacy and Safety of Tocilizumab in Adults With Rheumatoid Arthritis", ClinicalTrials.gov. Identifier: NCT01988012.
ClinicalTrials.gov. (May 11, 2016) "A Study to Compare Subcutaneous Versus Intravenous Administration of RoActemra/Actemra (Tocilizumab) in Participants With Moderate to Severe Active Rheumatoid Arthritis", ClinicalTrials.gov. Identifier: NCT01194414.
ClinicalTrials.gov. (Sep. 27, 2011) "Effect of SAR153191 (REGN88) With Methotrexate in Patients With Active Rheumatoid Arthritis Who Failed INF-a Blockers," Study Details, ClinicalTrials.gov Identifier: NCT01217814.
ClinicalTrials.gov. (Sep. 15, 2014) "Torpedo Study: A Study on Rapid Effect of Tocilizumab in Patients With Rheumatoid Arthritis With an Inadequate Response to Disease-Modifying Antirheumatic Drugs (DMARDs) or Anti-TNF", ClinicalTrials.gov. Identifier: NCT00977106.
Corraliza-Gorjón et al., "New strategies using antibody combinations to increase cancer treatment effectiveness", Frontiers in immunology, 2017, 8: 1804.
Emery et al., "Evidence-based review of biologic markers as indicators of disease progression and remission in rheumatoid arthritis", Rheumatol Int., Jul. 2007, 27(9): 793-806, Epublished May 16, 2007.
Genentech (Apr. 11, 2019) Actemra® (tocilizumab) injection, for intravenous or subcutaneous use.
Hashimoto et al., "Increase of Hemoglobin Levels by Anti-IL-6 Receptor Antibody (Tocilizumab) in Rheumatoid Arthritis", PLoS One, May 30, 2014, vol. 9, No. 5, pp. e98202: 1-7.
Heissigerova et al., "Efficacy and Safety of Sarilumab for the Treatment of Posterior Segment Noninfectious Uveitis (SARIL-NIU):: The Phase 2 Saturn Study", Ophthalmology, Mar. 2019, 126(3): 428-437.
Holm et al., "In diabetic retinopathy, foveal thickness of 300 mum seems to correlate with functionally significant loss of vision", Doc Ophthalmol., May 2007, 114(3): 117-124.
Huizen et al., "What does it mean if you have a high C-reactive protein level?", Medical News Today, Oct. 11, 2023.
Izumi et al., "Steroid-Sparing Effect of Tocilizumab and Methotrexate in Patients with Polymyalgia Rheumatica: A Retrospective Cohort Study", Journ Clin Med., Jun. 30, 2021, 10: 2948.
Kenny et al., "Therapeutic protein drug-drug interactions: navigating the knowledge gaps—highlights from the 2012 AAPS NBC Roundtable and IQ Consortium/FDA workshop", The AAPS Journal, 2013, 15(4): 933-940.
Lee, "A review of sarilumab for the treatment of rheumatoid arthritis", Immunotherapy, Oct. 18, 2017, 10(1): 57-65.
Mccreary et al., "Development and Validation of a Targeted Next-Generation Sequencing Gene Panel for Children With Neuroinflammation", JAMA Network Open, Oct. 30, 2019, 2(10): e1914274.
Mould et al., "Pharmacokinetics and pharmacodynamics of monoclonal antibodies", BioDrugs, 2010, 24(1): 23-39.
Ogata et al., "Phase III Study of the Efficacy and Safety of Subcutaneous Versus Intravenous Tocilizumab Monotherapy in Patients With Rheumatoid Arthritis", Arthritis Care & Research, Aug. 27, 2013, vol. 66, No. 3, pp. 344-354.
Ohta et al., "Mechanism-Based Approach Using a Biomarker Response to Evaluate Tocilizumab Subcutaneous Injection in Patients With Rheumatoid Arthritis With an Inadequate Response to Synthetic DMARDs (Matusri Study)", The Journal of Clinical Pharmacology, Jan. 2014, 54(1):109-119, Epublished Oct. 12, 2013 . . . .
Ohtsubo et al., "Effective combination therapy of TNF antagonists with DMARDs", Nihon Rinsho, Jul. 2007, 65(7): 1287-1291. In Japanese with English abstract.
Patel et al., "The Negative Effect of Carpal Tunnel Syndrome on Sleep Quality", Sleep Disorders, Feb. 17, 2014, Article ID 962746.
Paul et al., "Effectiveness of biologic and non-biologic antirheumatic drugs on anaemia markers in 153,788 patients with rheumatoid arthritis: New evidence from real-world data", Seminars in Arthritis and Rheumatism, Feb. 1, 2018, vol. 47, No. 4, pp. 478-484.
Prodanovic et al., "Matrix Metalloproteinases-3 Baseline Serum Levels in Early Rheumatoid Arthritis Patients without Initial Radiographic Changes: A TwoYear Ultrasonographic Study", Med Princ Pract., 2018, 27(4): 378-386, Epublished May 24, 2018.
Sack Jr. et al., "Serum amyloid A—a review", Mol Med., Aug. 30, 2018, 24(1): 46.
Sanofi KK, Kezvara for Subcutaneous Injection Report on the Deliberation Results, Pharmaceutical Evaluation Division, Pharmaceutical Safety and Environmental Health Bureau Ministry of Health, Labour, and Welfare, Non-proprietary Name: Sarilumab (genetical Recombination) (JAN), Date of Application: Oct. 7, 2016.
Santos et al., "Degree of decrease in central retinal thickness predicts visual acuity response to intravitreal ranibizumab in diabetic macular edema", Ophthalmologica, 2014, 231(1): 16-22.
Starkova et al., "ES02. Relationship between fatigue and IL 6, disease activity, depression in patients treated with tocilizumab", Rheumatology, Feb. 2012, 51(Suppl 1): i34-i41, Published Jan. 10, 2012.
Starkova et al., "Impact of tocilizumab therapy on fatigue in patients with rheumatoid arthritis", Scientific and Practical Rheumatology, 2012, N 52(3): 33-37, English translation included.
Strand et al., "Sustained benefit in rheumatoid arthritis following one course of rituximab: improvements in physical function over 2 years", Rheumatology, 2006, 45(12): 1505-1513.
Takeuchi, "Rheumatoid Arthritis: Advances in Diagnosis and Treatment", The Journal of the Japanese Society of Internal Medicine, 2012, vol. 101, pp. 2815-2817.
Tallarida et al., "Quantitative Methods for Assessing Drug Synergism", Genes & Cancer, 2011, 2(11): 1003-1008.
Targonska-Stepniak et al., "Serum Amyloid A as a Marker of Persistent Inflammation and an Indicator of Cardiovascular and Renal Involvement in Patients with Rheumatoid Arthritis", Mediators of Inflammation, Jan. 1, 2014.
Teper et al., "Update on the Management of Uveitic Macular Edema", J Clin Med., 2021, 10(18): 4133.
Tyagi et al., "Chemical Modification and Chemical Crosslinking for Protein/Enzyme Stabilization", Biokhimiya, 1998, 63(3): 395-407.
Unknown, "Differentiation of Arthritis: Advances in Diagnosis and Treatment 1. Rheumatoid Arthritis", The Journal of the Japanese Society of Internal Medicine, 2010, vol. 99, pp. 2392-2400.
Yukawa et al., "ACR2008 Recommendation: Treatment Strategy for rheumatoid arthritis based on ACR2008 recommendations", Journal of Clinical and Experimental Medicine, 2010, 234(1): 30-36. In Japanese.
"Highlights of Prescribing Information" for Actemra (tocilizumab), Reference ID: 5639738, Retrieved from url: <https://www.accessdata.fda.gov/drugsatfda_docs/label/2025/125276s149lbl.pdf>, Revised Aug. 2025.
"Highlights of Prescribing Information" for Kevzara (sarilumab), US Approval: 2017, Revised May 2025, Retrieved from url: <https://products.sanofi.us/kevzara/kevzara.pdf>.
Brunner et al., "Efficacy and safety of tocilizumab in patients with polyarticular-course juvenile idiopathic arthritis: results from a phase 3, randomised, double-blind withdrawal trial", Ann. Rheum. Dis., Jun. 2015, 74(6): 1110-1117.
Cell Signaling Technology, "Jak/Stat: IL-6 receptor signaling", Released Nov. 2012, including English translation, Obtained from url: <https://www.cellsignal.jp/pathways/jak-stat-il6-receptor-signaling>.
De Benedetti et al., "Sarilumab in Polyarticular-Course Juvenile Idiopathic Arthritis: Dose-Finding and 1-Year Analysis of a Phase 2b, Open-Label, Multicenter Study", Arthritis Care & Research, Nov. 14, 2025.
Den Broeder et al., "Non-Medical Switching from Tocilizumab to Sarilumab in Rheumatoid Arthritis Patients with Low Disease

(56) References Cited

OTHER PUBLICATIONS

Activity: An Observational Study", Clin Pharmacol Ther., Oct. 2023, 114(4): 810-814, Epublished Jul. 27, 2023.
Fleischmann et al., "Tocilizumab Inhibits Structural Joint Damage and Improves Physical Function in Patients with Rheumatoid Arthritis and Inadequate Responses to Methotrexate: Lithe Study 2-year Results", Journal of Rheumatology, Feb. 2013, 40(2): 113-126.
General guidelines for clinical evaluations of new drugs (Notification No. 43), issued in 1992 by New Drugs division, Pharmaceutical Affairs Bureau, Ministry of Health of Japan, Japanese language document, [https://www.pmda.go.jp/files/000206739.pdf].
Gill et al., "Multi-modal Imaging in Etanercept-induced Uveitis: A Case Series," The Open Ophthalmology Journal, 2020, 14: 70-74.
Knappik et al., "Fully synthetic human combinatorial antibody libraries (HuCAL) based on modular consensus frameworks and CDRs randomized with trinucleotides", Journ Mol Biol., Feb. 11, 2000, 296(1): 57-86.
Leclercq et al., "Efficacious switching from subcutaneous to intravenous tocilizumab in patients with non-infectious non-anterior uveitis," Journal of Ophthalmic Inflammation and Infection, Jul. 18, 2023, 13(1): 32.
Leipold et al., "Pharmacokinetic and Pharmacodynamic Considerations in the Design of Therapeutic Antibodies", Clin. Transl., Sci., Mar. 2019, 12(2): 130-139.
Onishi et al., "Comparative effectiveness of subcutaneous sarilumab 200 mg biweekly, subcutaneous Tocilizumab 162 mg biweekly, and intravenous Tocilizumab 8 mg/kg every 4 weeks in patients with rheumatoid arthritis: a prospective cohort study," Arthritis Res Ther., Mar. 7, 2025, 27(1): 52.
Pillar et al., "Evaluating the Effectiveness of Escalating to Weekly Adalimumab Dosing for the Treatment of Non-infectious Uveitis: A Multi-Center Study," American Academy of Ophthalmology, Sep. 30, 2025, S0161-6420(25)00606-2.
Rabia et al., "Understanding and overcoming trade-offs between antibody affinity, specificity, stability and solubility", Biochem Eng J., Sep. 15, 2018, 137: 365-374.
Saito et al., "Differences in the strength of inhibition of interleukin-6 signalling by subcutaneous sarilumab and tocilizumab in rheumatoid arthritis patients," Clinical and Experimental Rheumatology, Jul. 2023, 41(7): 1451-1455.
Swets et al., "A comparison of the effectiveness of different doses of tocilizumab and sarilumab in the treatment of severe COVID-19: a natural experiment due to drug shortages", International Journal of Infectious Diseases, Apr. 2023, 129: 57-62.
Uhlig et al., "Quantification of reduced health-related quality of life in patients with rheumatoid arthritis compared to the general population", J Rheumatol., Jun. 2007, 34(6): 1241-1247, Epublished May 15, 2007.
Xu et al., "Modeling, Simulation, and Extrapolation to Optimize Pediatric Development Plan: Sarilumab Polyarticular-Course Juvenile Arthritis Application", Journal of Pharmacokinetics and Pharmacodynamics, Mar. 24, 2026, 53:19.
Yokota et al., "Efficacy, safety and tolerability of tocilizumab in patients with systemic juvenile idiopathic arthritis", Ther. Adv. Musculoskelet. Dis., Dec. 2012;4(6):387-397.

* cited by examiner

SEQUENCE LISTING

```
<160> NUMBER OF SEQ ID NOS: 11

<210> SEQ ID NO 1
<211> LENGTH: 116
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 1

Glu Val Gln Leu Val Glu Ser Gly Gly Gly Leu Val Gln Pro Gly Arg
1               5                   10                  15

Ser Leu Arg Leu Ser Cys Ala Ala Ser Arg Phe Thr Phe Asp Asp Tyr
            20                  25                  30

Ala Met His Trp Val Arg Gln Ala Pro Gly Lys Gly Leu Glu Trp Val
```

```
        35                  40                  45

Ser Gly Ile Ser Trp Asn Ser Gly Arg Ile Gly Tyr Ala Asp Ser Val
    50                  55                  60

Lys Gly Arg Phe Thr Ile Ser Arg Asp Asn Ala Glu Asn Ser Leu Phe
65                  70                  75                  80

Leu Gln Met Asn Gly Leu Arg Ala Glu Asp Thr Ala Leu Tyr Tyr Cys
                85                  90                  95

Ala Lys Gly Arg Asp Ser Phe Asp Ile Trp Gly Gln Gly Thr Met Val
            100                 105                 110

Thr Val Ser Ser
        115


<210> SEQ ID NO 2
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 2

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Gly Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Ser Tyr Tyr Cys Gln Gln Ala Asn Ser Phe Pro Tyr
                85                  90                  95

Thr Phe Gly Gln Gly Thr Lys Leu Glu Ile Lys
            100                 105


<210> SEQ ID NO 3
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 3

Arg Phe Thr Phe Asp Asp Tyr Ala
1               5


<210> SEQ ID NO 4
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 4

Ile Ser Trp Asn Ser Gly Arg Ile
1               5
```

<210> SEQ ID NO 5
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 5

Ala Lys Gly Arg Asp Ser Phe Asp Ile
1 5

<210> SEQ ID NO 6
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 6

Gln Gly Ile Ser Ser Trp
1 5

<210> SEQ ID NO 7
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 7

Gly Ala Ser
1

<210> SEQ ID NO 8
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 8

Gln Gln Ala Asn Ser Phe Pro Tyr Thr
1 5

<210> SEQ ID NO 9
<211> LENGTH: 446
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 9

Glu Val Gln Leu Val Glu Ser Gly Gly Gly Leu Val Gln Pro Gly Arg
1 5 10 15

Ser Leu Arg Leu Ser Cys Ala Ala Ser Arg Phe Thr Phe Asp Asp Tyr
20 25 30

-continued

```
Ala Met His Trp Val Arg Gln Ala Pro Gly Lys Gly Leu Glu Trp Val
        35                  40                  45

Ser Gly Ile Ser Trp Asn Ser Gly Arg Ile Gly Tyr Ala Asp Ser Val
    50                  55                  60

Lys Gly Arg Phe Thr Ile Ser Arg Asp Asn Ala Glu Asn Ser Leu Phe
65                  70                  75                  80

Leu Gln Met Asn Gly Leu Arg Ala Glu Asp Thr Ala Leu Tyr Tyr Cys
                85                  90                  95

Ala Lys Gly Arg Asp Ser Phe Asp Ile Trp Gly Gln Gly Thr Met Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445
```

<210> SEQ ID NO 10
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 10

Asp Ile Gln Met Thr Gln Ser Pro Ser Ser Val Ser Ala Ser Val Gly
1 5 10 15

Asp Arg Val Thr Ile Thr Cys Arg Ala Ser Gln Gly Ile Ser Ser Trp
20 25 30

Leu Ala Trp Tyr Gln Gln Lys Pro Gly Lys Ala Pro Lys Leu Leu Ile
35 40 45

Tyr Gly Ala Ser Ser Leu Glu Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Ser Tyr Tyr Cys Gln Gln Ala Asn Ser Phe Pro Tyr
85 90 95

Thr Phe Gly Gln Gly Thr Lys Leu Glu Ile Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Cys
210

<210> SEQ ID NO 11
<211> LENGTH: 358
<212> TYPE: PRT
<213> ORGANISM: Homo sapiens

<400> SEQUENCE: 11

Met Val Ala Val Gly Cys Ala Leu Leu Ala Ala Leu Leu Ala Ala Pro
1 5 10 15

Gly Ala Ala Leu Ala Pro Arg Arg Cys Pro Ala Gln Glu Val Ala Arg
20 25 30

Gly Val Leu Thr Ser Leu Pro Gly Asp Ser Val Thr Leu Thr Cys Pro
35 40 45

Gly Val Glu Pro Glu Asp Asn Ala Thr Val His Trp Val Leu Arg Lys
50 55 60

Pro Ala Ala Gly Ser His Pro Ser Arg Trp Ala Gly Met Gly Arg Arg
65 70 75 80

Leu Leu Leu Arg Ser Val Gln Leu His Asp Ser Gly Asn Tyr Ser Cys
85 90 95

-continued

```
Tyr Arg Ala Gly Arg Pro Ala Gly Thr Val His Leu Leu Val Asp Val
            100                 105                 110

Pro Pro Glu Glu Pro Gln Leu Ser Cys Phe Arg Lys Ser Pro Leu Ser
        115                 120                 125

Asn Val Val Cys Glu Trp Gly Pro Arg Ser Thr Pro Ser Leu Thr Thr
    130                 135                 140

Lys Ala Val Leu Leu Val Arg Lys Phe Gln Asn Ser Pro Ala Glu Asp
145                 150                 155                 160

Phe Gln Glu Pro Cys Gln Tyr Ser Gln Glu Ser Gln Lys Phe Ser Cys
                165                 170                 175

Gln Leu Ala Val Pro Glu Gly Asp Ser Ser Phe Tyr Ile Val Ser Met
            180                 185                 190

Cys Val Ala Ser Ser Val Gly Ser Lys Phe Ser Lys Thr Gln Thr Phe
        195                 200                 205

Gln Gly Cys Gly Ile Leu Gln Pro Asp Pro Pro Ala Asn Ile Thr Val
    210                 215                 220

Thr Ala Val Ala Arg Asn Pro Arg Trp Leu Ser Val Thr Trp Gln Asp
225                 230                 235                 240

Pro His Ser Trp Asn Ser Ser Phe Tyr Arg Leu Arg Phe Glu Leu Arg
                245                 250                 255

Tyr Arg Ala Glu Arg Ser Lys Thr Phe Thr Thr Trp Met Val Lys Asp
            260                 265                 270

Leu Gln His His Cys Val Ile His Asp Ala Trp Ser Gly Leu Arg His
        275                 280                 285

Val Val Gln Leu Arg Ala Gln Glu Glu Phe Gly Gln Gly Glu Trp Ser
    290                 295                 300

Glu Trp Ser Pro Glu Ala Met Gly Thr Pro Trp Thr Glu Ser Arg Ser
305                 310                 315                 320

Pro Pro Ala Glu Asn Glu Val Ser Thr Pro Met Gln Ala Leu Thr Thr
                325                 330                 335

Asn Lys Asp Asp Asp Asn Ile Leu Phe Arg Asp Ser Ala Asn Ala Thr
            340                 345                 350

Ser Leu Pro Val Gln Asp
        355
```

COMPOSITIONS AND METHODS FOR TREATING NONINFLAMMATORY PAIN IN SUBJECTS WITH RHEUMATOID ARTHRITIS

RELATED APPLICATIONS

This application is a 35 U.S.C. § 371 filing of International Patent Application No. PCT/IB2021/054652, filed May 27, 2021, which claims priority to U.S. Provisional Patent Application Ser. Nos. 63/032,035, filed May 29, 2020, and 63/077,378, filed Sep. 11, 2020, and EP Provisional Patent Application Serial No. 21315081.6, filed May 11, 2021. The entire disclosure of each of these applications is hereby incorporated herein by reference in its entirety.

SEQUENCE LISTING

The instant application contains a Sequence Listing which has been submitted electronically in ASCII format and is hereby incorporated by reference in its entirety. Said ASCII copy, created on Nov. 17, 2022, is named 735043 SA9-294US ST25.txt and is 13, 142 bytes in size.

FIELD

The present disclosure relates to the field of therapeutic treatment of non-inflammatory pain in subjects who have or who have had rheumatoid arthritis.

BACKGROUND

Rheumatoid arthritis (RA) is the most common form of autoimmune inflammatory arthritis, affecting about 1% of the population. It is an autoimmune disease in which the body's immune system attacks the lining of the membranes that surround joints. RA causes chronic inflammation which can result in joint pain, swelling and stiffness. Pain is a core-set domain and a troubling symptom to patients with RA, and may be directly related to inflammation; however, noninflammatory pain (NIP) is also common in patients with RA.

Sarilumab is an interleukin-6 receptor antagonist for treatment of adults with moderately to severely active RA with an inadequate response or intolerance to one or more disease-modifying antirheumatic drugs (DMARDs).

SUMMARY

This disclosure provides methods and compositions for treating NIP in a subject who has rheumatoid arthritis. In various embodiments, treating the subject comprises administering a therapeutically effective amount of an antibody that specifically binds IL-6R.

In one aspect, the disclosure provides methods for treating non-inflammatory pain (NIP) in a subject in need thereof with rheumatoid arthritis, comprising administering to the subject a therapeutically effective dose of an antibody that specifically binds IL-6 receptor, wherein the antibody comprises a heavy chain variable region comprising complementarity determining regions HCDR1, HCDR2, and HCDR3 and a light chain variable region comprising complementary determining regions LCDR1, LCDR2, and LCDR3, wherein: HCDR1 comprises the amino acid sequence of SEQ ID NO: 3; HCDR2 comprises the amino acid sequence of SEQ ID NO: 4; HCDR3 comprises the amino acid sequence of SEQ ID NO: 5; LCDR1 comprises the amino acid sequence of SEQ ID NO: 6; LCDR2 comprises the amino acid sequence of SEQ ID NO: 7; and LCDR3 comprises the amino acid sequence of SEQ ID NO: 8. In various embodiments, the antibody that specifically binds to the IL-6 receptor comprises a heavy chain variable region sequence SEQ ID NO: 1 and a light chain variable region sequence of SEQ ID NO: 2. In various embodiments, the subject has a tender joint count (TJC) of at least 21. In various embodiments, the tender joint count differs from a swollen joint count by at least 5. In various embodiments, the antibody is administered subcutaneously. In various embodiments, the subject is administered a dose of about 150 mg or about 200 mg of the antibody. In various embodiments, the antibody is administered to the subject at least once every two weeks. In various embodiments, the subject has moderately to severely active rheumatoid arthritis. In various embodiments, the subject is not administered any other DMARD in course of administration with the antibody. In various embodiments, the subject is also administered one or more additional DMARDs with the antibody. In various embodiments, the one or more additional DMARDs comprise methotrexate. In various embodiments, the one or more additional DMARDs comprise a TNF antagonist. In various embodiments, the TNF antagonist is selected from the group consisting of etanercept, infliximab, adalimumab, golimumab and certolizumab pegol. In various embodiments, the subject was previously ineffectively treated for rheumatoid arthritis by administering at least one DMARD distinct from the antibody. In various embodiments, the DMARD is methotrexate. In various embodiments, the DMARD is a TNF antagonist. In various embodiments, the TNF antagonist is selected from the group consisting of etanercept, infliximab, adalimumab, golimumab and certolizumab pegol. In various embodiments, the subject is intolerant of one or more DMARDs, or wherein the subject is considered an inappropriate candidate for continued treatment with one or more DMARDs. In various embodiments, the subject has had an inadequate response to one or more DMARDs. In various embodiments, the DMARD is methotrexate. In various embodiments, the DMARD is a TNF antagonist. In various embodiments, the TNF antagonist is selected from the group consisting of etanercept, infliximab, adalimumab, golimumab and certolizumab pegol.

In another aspect, the present disclosure provides methods for treating NIP in a subject in need thereof, comprising selecting a subject who has rheumatoid arthritis and NIP; and administering to the subject a therapeutically effective dose of an antibody that specifically binds IL-6 receptor, wherein the antibody comprises a heavy chain variable region comprising complementarity determining regions HCDR1, HCDR2, and HCDR3 and a light chain variable region comprising complementary determining regions LCDR1, LCDR2, and LCDR3, wherein: HCDR1 comprises the amino acid sequence of SEQ ID NO: 3; HCDR2 comprises the amino acid sequence of SEQ ID NO: 4; HCDR3 comprises the amino acid sequence of SEQ ID NO: 5; LCDR1 comprises the amino acid sequence of SEQ ID NO: 6; LCDR2 comprises the amino acid sequence of SEQ ID NO: 7; and LCDR3 comprises the amino acid sequence of SEQ ID NO: 8. In various embodiments, the antibody that specifically binds to the IL-6 receptor comprises a heavy chain variable region sequence SEQ ID NO: 1 and a light chain variable region sequence of SEQ ID NO: 2. In various embodiments, the subject has a TJC of at least 21. In various embodiments, the tender joint count differs from a swollen joint count by at least 5. In various embodiments, the antibody is administered subcutaneously. In various embodiments, the subject is administered a dose of about 150 mg or about 200 mg of the antibody. In various embodiments, the antibody is administered to the subject at least once every two weeks. In various embodiments, the subject has moderately to severely active rheumatoid arthritis. In various embodiments, the subject is not administered any other DMARD in course of administration with the antibody. In various embodiments, the subject is also administered one or more additional DMARDs with the antibody. In various embodiments, the one or more additional DMARDs comprise methotrexate. In various embodiments, the one or more additional DMARDs comprise a TNF antagonist. In various embodiments, the TNF antagonist is selected from the group consisting of etanercept, infliximab, adalimumab, golimumab and certolizumab pegol. In various embodiments, the subject was previously ineffectively treated for rheumatoid arthritis by administering at least one DMARD distinct from the antibody. In various embodiments, the DMARD is methotrexate. In various embodiments, the DMARD is a TNF antagonist. In various embodiments, the TNF antagonist is selected from the group consisting of etanercept, infliximab, adalimumab, golimumab and certolizumab pegol. In various embodiments, the subject is intolerant of one or more DMARDs, or wherein the subject is considered an inappropriate candidate for continued treatment with one or more DMARDs. In various embodiments, the subject has had an inadequate response to one or more DMARDs. In various embodiments, the DMARD is methotrexate. In various embodiments, the DMARD is a TNF antagonist. In various embodiments, the TNF antagonist is selected from the group consisting of etanercept, infliximab, adalimumab, golimumab and certolizumab pegol.

In another aspect, the present disclosure provides antibodies for use in treating NIP in a patient in need thereof with rheumatoid arthritis, wherein the antibodies specifically bind IL-6 receptor, and wherein the antibodies comprise a heavy chain variable region comprising complementarity determining regions HCDR1, HCDR2, and HCDR3 and a light chain variable region comprising complementary determining regions LCDR1, LCDR2, and LCDR3, wherein: HCDR1 comprises the amino acid sequence of SEQ ID NO: 3; HCDR2 comprises the amino acid sequence of SEQ ID NO: 4; HCDR3 comprises the amino acid sequence of SEQ ID NO: 5; LCDR1 comprises the amino acid sequence of SEQ ID NO: 6; LCDR2 comprises the amino acid sequence of SEQ ID NO: 7; and LCDR3 comprises the amino acid sequence of SEQ ID NO: 8. In various embodiments, the antibody specifically binds to the IL-6 receptor comprises a heavy chain variable region sequence SEQ ID NO: 1 and a light chain variable region sequence of SEQ ID NO: 2. In various embodiments, the subject has a TJC of at least 21. In various embodiments, the tender joint count differs from a swollen joint count by at least 5. In various embodiments, the antibody is administered subcutaneously. In various embodiments, the subject is administered a dose of about 150 mg or about 200 mg of the antibody. In various embodiments, the antibody is administered to the subject at least once every two weeks. In various embodiments, the subject has moderately to severely active rheumatoid arthritis. In various embodiments, the subject is not administered with any other DMARD in course of administration with the antibody. In various embodiments, the subject is also administered one or more additional DMARDs with the antibody. In various embodiments, the one or more additional DMARDs comprise methotrexate. In various embodiments, the one or more additional DMARDs comprise a TNF antagonist. In various embodiments, the TNF antagonist is selected from the group consisting of etanercept, infliximab, adalimumab, golimumab and certolizumab pegol. In various embodiments, the subject was previously ineffectively treated for rheumatoid arthritis by administering at least one DMARD different from the antibody. In various embodiments, the DMARD is methotrexate. In various embodiments, the DMARD is a TNF antagonist. In various embodiments, the TNF antagonist is selected from the group consisting of etanercept, infliximab, adalimumab, golimumab and certolizumab pegol. In various embodiments, the subject is intolerant of one or more DMARDs, or wherein the subject is considered an inappropriate candidate for continued treatment with one or more DMARDs. In various embodiments, the subject is has had an inadequate response to one or more DMARDs. In various embodiments, the DMARD is methotrexate. In various embodiments, the DMARD is a TNF antagonist. In various embodiments, the TNF antagonist is selected from the group consisting of etanercept, infliximab, adalimumab, golimumab and certolizumab pegol.

BRIEF DESCRIPTION OF THE FIGURES

The foregoing and other features and advantages of the present invention will be more fully understood from the following detailed description of illustrative embodiments taken in conjunction with the accompanying drawings.

DETAILED DESCRIPTION

Figure 1:
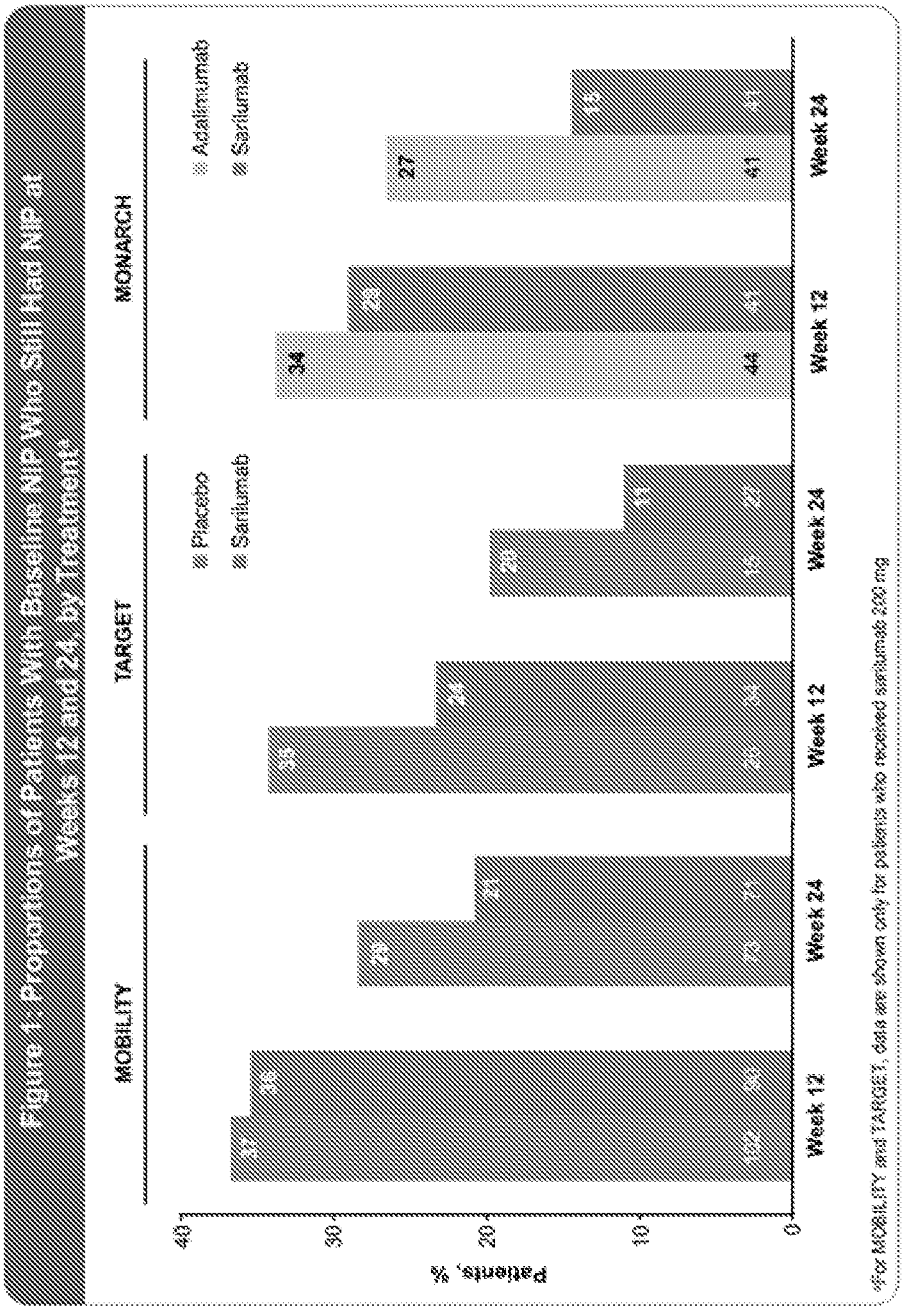
FIG. 1 shows percentage of patients who had NIP by week 12 and 24, by treatment.

Inflammation is a key driver of pain in rheumatoid arthritis (RA). However, some patients experience more pain than would be expected based on the amount of synovitis observed, which may indicate the presence of noninflammatory pain (NIP). This disclosure provides pharmaceutical compositions and methods of using these compositions for the treatment of NIP in subjects with RA. These compositions and methods include at least one antibody that specifically binds interleukin-6 receptor (hIL-6R).

As used within the claims, the Summary, and the Detailed Description herein, the term "about" in quantitative terms refers to plus or minus 10% of the value it modifies (rounded up to the nearest whole number if the value is not subdividable, such as a number of molecules or nucleotides). For example, the phrase "about 100 mg" would encompass 90 mg to 110 mg, inclusive; the phrase "about 2500 mg" would encompass 2250 mg to 2750 mg. When applied to a percentage, the term "about" refers to plus or minus 10% relative to that percentage. For example, the phrase "about 20%" would encompass 18-22% and "about 80%" would encompass 72-88%, inclusive. Moreover, where "about" is used herein in conjunction with a quantitative term it is understood that in addition to the value plus or minus 10%, the exact value of the quantitative term is also contemplated and described. For example, the term "about 23%" expressly contemplates, describes, and includes exactly 23%.

It is to be noted that the term "a" or "an" entity refers to one or more of that entity; for example, "a symptom," is understood to represent one or more symptoms. As such, the terms "a" (or "an"), "one or more," and "at least one" can be used interchangeably herein.

Furthermore, "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B and/or C" is intended to encompass each of the following aspects: A, B and C; A, B or C; A or C; A or B; B or C; A and C; A and B; B and C; A (alone); B (alone); and C (alone).

It is understood that wherever aspects are described herein with the language "comprising," otherwise analogous aspects described in terms of "consisting of" and/or "consisting essentially of" are also provided.

The term "pain" refers to discomfort caused by intense or damaging stimuli, including illness, injury, or mental anguish. In some embodiments, pain has both physical and emotional components and it is experienced as an unpleasant sensation that can range from mild, localized discomfort to agony.

As used herein, "acute pain" refers to pain that lasts less than 3 months. In some embodiments, acute pain is associated with soft tissue damage and gradually resolves as the damage heals. Acute pain is detected by specialized nerve receptors (nociceptors) that detect and respond to strong signals that relay information about danger to the organism, presumably so that the organism can mobilize defenses. In RA, persistent signaling from within inflamed joints can lead to lowering of the threshold for stimulation of nociceptors with resultant hypersensitivity to nociceptive stimulation (peripheral sensitization). It is likely that local factors, such as cytokines, may exert direct, noninflammatory effects on sensory neurons.

The term "chronic pain" refers to pain that lasts at least 3 months. In some embodiments, chronic pain is described as pain that extends beyond the expected period of healing. In some embodiments, chronic pain includes unanticipated prolonged pain in patients with RA who appear to be in remission. Chronic pain is often associated with central sensitization and may be a manifestation of aberrant neuronal activity from peripheral sensitization of primary sensory neurons and subsequent or additional sensitization of neurons in the CNS. There may be little or no relationship to prior or current inflammation in this state.

The term "non-inflammatory pain" or "NIP" refers to pain not associated with inflammation, as described above. In some cases, the NIP may be due to arthralgia or polyarthralgia. NIP typically presents with an absence of systemic symptoms such as fever or weight loss. NIP can also present without swelling or warmth. NIP can also be characterized by minimal morning stiffness which is intermittent, lasts less than 60 minutes and/or stiffness which is made worse, not improved, by activity. In some embodiments, NIP includes acute or chronic pain. In some embodiments, NIP includes allodynia, enhanced pain and neuropathic pain. In some embodiments, a subject with NIP also is experiencing central sensitization. In some embodiments, subjects with NIP are earlier in the course of RA. In some embodiments, these subjects have not been diagnosed with RA and do not show symptoms of inflammation. In some embodiments, subjects with NIP have extra-articular or diffuse pain.

As used herein, "central sensitization" refers to anomalies in spinal and brain pain processing which result in increased pain sensitivity at diffuse sites and result in a heightened overall response state throughout the central nervous system (CNS) in response to sensory impulses, which are interpreted in the brain through a complex filter as enhanced pain. This category may include psychosocial interplay with pain perception to a chronic pain state. In central sensitization, new nociceptive pathways are created, for example, by recruiting mechanoreceptors to conduct pain. This occurs mainly by producing increased sensitization in the spine and, in time, this state can become self-perpetuating even in the absence of injury, and unrelated to any protective purpose.

Thus, in some embodiments, in a patient with underlying inflammatory pain from RA which might intrinsically cause mild pain only. As used herein, "hyperalgesia" or "enhanced pain" refers to relatively mild pain that is exaggerated and experienced as a much more intense pain. Sensations of pain in this state may also be produced from usually nonpainful stimuli such as movement (for example, making a fist) which are normally interpreted as informational inputs. As used herein, "allodynia" refers to pain that results from typically nonpainful stimuli. Clinical observation suggests a disconnect between pain and inflammation in some cases of early RA, for example, bilateral symmetrical small arthralgias can occur prior to any objective evidence of joint inflammation. Conversely, some patients with RA may present with joint inflammation (and joint damage) only, without pain (the "robust rheumatoid" type). In some embodiments, there is a spectrum of RA presentation with phenotypes ranging from patients with mainly identifiable synovitis with accompanying pain to those who present with pain only. Attempts have been made to identify these latter patients with RA who have noninflammatory pain earlier in the course of disease, for example through the use of the swollen to tender joint count ratio.

Discordance between patient self-reported pain and objective evaluation of inflammation has been reported, and patient-reported pain appears to correlate poorly with physicians' assessments and measures of inflammation across studies. The view that pain is not solely derived from inflammation is also supported by observations that anti-cytokine treatments produce pain relief well before reduction in inflammation, and that residual pain persists in some 12-50% of patients in remission, and in 82% of patients with "somewhat to completely controlled" disease following treatment of the inflammatory component of RA. Rheumatologists often attribute this residual pain to fibromyalgia or to underlying joint damage from RA, but the latter explanation seems unlikely given radiographic damage has been shown to account for only 2.1% of patient-reported pain. The proportion of patients with RA fulfilling fibromyalgia classification criteria increases also throughout the course of disease progression, which again suggests central pain augmentation.

RA is a disease involving joints, but, in some embodiments, pain is often reported as being extra-articular and it may be diffuse, with widespread achiness in remote, non-articular sites as well as in joints, and can vary in location and time. This pain does not appear to be related to synovitis and is likely due to alteration of central pain processing. To the perceptive clinician there are sometimes clues hinting that aspects of pain in patients with RA may derive from nervous system involvement, for example, when sensations of pain are reported as tingling, burning, or as sharp. CNS involvement is getting clearer; a substantial proportion of patients with RA have some form of identifiable neuropathic involvement. Autonomic neuropathy too is increasingly identified as associated with RA. As such, in some embodiments the CNS is a significant associated organ system in RA.

The many clinically apparent dissociations between pain and inflammation suggests some RA pain may be an independent problem overlapping with, but not solely due to inflammation with multiple mechanisms involved. In some embodiments, patient pain in RA originates with some form of inflammation or injury, but, in addition, RA patients feel pain that is also concurrently and independently triggered (with no or minor sensory stimulation), passed on by the peripheral nervous system, amplified in the spinal cord and experienced in the CNS. In the brain, the sensations from more distally are interwoven with external psychosocial factors. Indeed, pain has been described as "an opinion." In various embodiments, this pain is a distinct entity from the pain of inflammation, and this form of pain is at least partly due to aberrancies related to cytokine dysregulation.

In some embodiments, cytokines cause joint inflammation (which in turn causes pain), but there can be other effects of cytokines on peripheral and also other parts of the nervous system that lead to pain more directly, and do not necessarily correlate with inflammation. In some embodiments, the cytokine IL-6 plays an important role in this.

In some embodiments, NIP is defined as a difference between the 28-joint tender joint count (TJC) and swollen joint count (SJC), using the established formula: TJC−SJC≥7.

In some embodiments, pain experienced in the previous week is measured. In some embodiments, pain experienced in the previous 2, 3, 4, 5, 6, 7, 8 or more weeks is measured. In some embodiments, pain experienced in the previous month is measured. In some embodiments, pain experienced in the previous, 2, 3, 4, 5, 6, 7, 8, 9, 10, 11, 12 or more months is measured. In some embodiments, pain experienced in the previous year is measured. In some embodiments, pain experienced for the previous 2, 3, 4, 5, 6, 7, 8, 9, 10 or more years is measured.

IL-6 interacts directly with the IL-6Rα subunit and the IL-6/IL-6Rα pair forms a high affinity complex with the glycoprotein 130 (gp130) subunit and initiates intracellular signaling via the Janus kinase (JAK)-signal transducer and activator of transcription (STAT) (JAK/STAT) and Ras Raf-mitogen-activated protein kinase (MAPK) pathways. IL-6Rα also exists in a soluble form, which is involved in trans-signaling and allows IL-6 to affect cells that do not express IL-6Rα including synovial cells in the joint.

Sarilumab (SAR153191), also designated as REGN88, is a recombinant IgG1 kappa monoclonal antibody of fully human sequence directed against the alpha subunit of the IL-6 receptor complex (IL-6Rα). Sarilumab blocks the binding of IL-6 and interrupts the cytokine-mediated signaling cascade.

Antibodies

The present disclosure includes methods that comprise administering to a subject an antibody, or an antigen-binding fragment thereof, that binds specifically to hIL-6R. As used herein, the term "hIL-6R" means a human cytokine receptor that specifically binds human interleukin-6 (IL-6). In certain embodiments, the antibody that is administered to the patient binds specifically to the extracellular domain of hIL-6R.

The term "antibody," as used herein, refers to immunoglobulin molecules comprising four polypeptide chains, two heavy (H) chains and two light (L) chains inter-connected by disulfide bonds, as well as multimers thereof (e.g., IgM). Each heavy chain comprises a heavy chain variable region (abbreviated herein as HCVR or VH) and a heavy chain constant region. The heavy chain constant region comprises three domains, CH1, CH2 and CH3. Each light chain comprises a light chain variable region (abbreviated herein as LCVR or VL) and a light chain constant region. The light chain constant region comprises one domain (CL1). The VH and VL regions can be further subdivided into regions of hypervariability, termed complementarity determining regions (CDRs), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. In some embodiments, the FRs of the antibody (or antigen-binding portion thereof) may be identical to the human germline sequences, or may be naturally or artificially modified. An amino acid consensus sequence may be defined based on a side-by-side analysis of two or more CDRs.

The term "antibody," as used herein, also includes antigen-binding fragments of full antibody molecules. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and optionally constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of antigen-binding fragments include: (i) Fab fragments; (ii) F(ab')2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g., monovalent nanobodies, and bivalent nanobodies), small modular immunopharmaceuticals (SMIPs), and shark variable IgNAR domains, are also encompassed within the expression "antigen-binding fragment," as used herein.

An antigen-binding fragment of an antibody will typically comprise at least one variable domain. The variable domain may be of any size or amino acid composition and will generally comprise at least one CDR which is adjacent to or in frame with one or more framework sequences. In antigen-binding fragments having a VH domain associated with a VL domain, the VH and VL domains may be situated relative to one another in any suitable arrangement. For example, the variable region may be dimeric and contain VH-VH, VH-VL or VL-VL dimers. Alternatively, the antigen-binding fragment of an antibody may contain a monomeric VH or VL domain.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody include: (i) VH-CH1; (ii) VH-CH2; (iii) VH-CH3; (iv) VH-CH1-CH2; (v) VH-CH1-CH2-CH3; (vi) VH-CH2-CH3; (vii) VH-CL; (viii) VL-CH1; (ix) VL-CH2; (x) VL-CH3; (xi) VL-CH1-CH2; (xii) VL-CH1-CH2-CH3; (xiii) VL-CH2-CH3; and (xiv) VL-CL. In any configuration of variable and constant domains, including any of the exemplary configurations listed above, the variable and constant domains may be either directly linked to one another or may be linked by a full or partial hinge or linker region. A hinge region may in various embodiments consist of at least 2 (e.g., 5, 10, 15, 20, 40, 60 or more) amino acids which result in a flexible or semi-flexible linkage between adjacent variable and/or constant domains in a single polypeptide molecule. Moreover, an antigen-binding fragment of an antibody may in various embodiments comprise a homodimer or hetero-dimer (or other multimer) of any of the variable and constant domain configurations listed above in non-covalent association with one another and/or with one or more monomeric VH or VL domain (e.g., by disulfide bond(s)).

In certain embodiments, the antibody or antibody fragment for use in a method disclosed herein may be a monospecific antibody. In certain embodiments, the antibody or antibody fragment for use in a method disclosed herein may be a multispecific antibody, which may be specific for different epitopes of one target polypeptide or may contain antigen-binding domains specific for epitopes of more than one target polypeptide. An exemplary bispecific antibody format that can be used in the context certain embodiments involves the use of a first immunoglobulin (Ig) CH3 domain and a second Ig CH3 domain, wherein the first and second Ig CH3 domains differ from one another by at least one amino acid, and wherein at least one amino acid difference reduces binding of the bispecific antibody to Protein A as compared to a bi-specific antibody lacking the amino acid difference. In one embodiment, the first Ig CH3 domain binds Protein A and the second Ig CH3 domain contains a mutation that reduces or abolishes Protein A binding such as an H95R modification (by IMGT exon numbering; H435R by EU numbering). The second CH3 may further comprise an Y96F modification (by IMGT; Y436F by EU). Further modifications that may be found within the second CH3 include: D16E, L18M, N44S, K52N, V57M, and V82I (by IMGT; D356E, L358M, N384S, K392N, V397M, and V422I by EU) in the case of IgG1 antibodies; N44S, K52N, and V82I (IMGT; N384S, K392N, and V422I by EU) in the case of IgG2 antibodies; and Q15R, N44S, K52N, V57M, R69K, E79Q, and V82I (by IMGT; Q355R, N384S, K392N, V397M, R409K, E419Q, and V422I by EU) in the case of IgG4 antibodies. Variations on the bi-specific antibody format described above are contemplated within the scope of certain embodiments. Any multispecific antibody format, including the exemplary bispecific antibody formats disclosed herein, may in various embodiments be adapted for use in the context of an antigen-binding fragment of an anti-IL-6R antibody using routine techniques available in the art.

The fully-human anti-IL-6R antibodies disclosed herein may comprise one or more amino acid substitutions, insertions and/or deletions in the framework and/or CDR regions of the heavy and light chain variable domains as compared to the corresponding germline sequences. Such mutations can be readily ascertained by comparing the amino acid sequences disclosed herein to germline sequences available from, for example, public antibody sequence databases. The present disclosure includes antibodies, and antigen-binding fragments thereof, which are derived from any of the amino acid sequences disclosed herein, wherein one or more amino acids within one or more framework and/or CDR regions are back-mutated to the corresponding germline residue(s) or to a conservative amino acid substitution (natural or non-natural) of the corresponding germline residue(s)(such sequence changes are referred to herein as "germline back-mutations"). A person of ordinary skill in the art, starting with the heavy and light chain variable region sequences disclosed herein, can easily produce numerous antibodies and antigen-binding fragments which comprise one or more individual germline back-mutations or combinations thereof. In certain embodiments, all of the framework residues and/or CDR residues within the VH and/or VL domains are mutated back to the germline sequence. In other embodiments, only certain residues are mutated back to the germline sequence, e.g., only the mutated residues found within the first 8 amino acids of FR1 or within the last 8 amino acids of FR4, or only the mutated residues found within CDR1, CDR2 or CDR3. Furthermore, included herein are antibodies that may contain any combination of two or more germline back-mutations within the framework and/or CDR regions, i.e., wherein certain individual residues are mutated back to the germline sequence while certain other residues that differ from the germline sequence are maintained. Once obtained, antibodies and antigen-binding fragments that contain one or more germline back-mutations can be easily tested for one or more desired property such as, improved binding specificity, increased binding affinity, improved or enhanced antagonistic or agonistic biological properties (as the case may be), reduced immunogenicity, etc. Antibodies and antigen-binding fragments obtained in this general manner are encompassed within the present disclosure.

The constant region of an antibody is important in the ability of an antibody to fix complement and mediate cell-dependent cytotoxicity. Thus, the isotype of an antibody may be selected on the basis of whether it is desirable for the antibody to mediate cytotoxicity.

The term "human antibody," as used herein, is intended to include antibodies having variable and constant regions derived from human germline immunoglobulin sequences. The human antibodies featured in the disclosure may in various embodiments nonetheless include amino acid residues not encoded by human germline immunoglobulin sequences (e.g., mutations introduced by random or site-specific mutagenesis in vitro or by somatic mutation in vivo), for example in the CDRs and in some embodiments CDR3. However, the term "human antibody," as used herein, is not intended to include antibodies in which CDR sequences derived from the germline of another mammalian species, such as a mouse, have been grafted onto human framework sequences.

The term "recombinant human antibody," as used herein, is intended to include all human antibodies that are prepared, expressed, created or isolated by recombinant means, such as antibodies expressed using a recombinant expression vector transfected into a host cell (described further below), antibodies isolated from a recombinant, combinatorial human antibody library (described further below), antibodies isolated from an animal (e.g., a mouse) that is transgenic for human immunoglobulin genes or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo.

Human antibodies can exist in two forms that are associated with hinge heterogeneity. In an embodiment, an immunoglobulin molecule comprises a stable four chain construct of approximately 150-160 kDa in which the dimers are held together by an interchain heavy chain disulfide bond. In another embodiment, the dimers are not linked via inter-chain disulfide bonds and a molecule of about 75-80 kDa is formed composed of a covalently coupled light and heavy chain (half-antibody). In certain embodiments, these forms have been extremely difficult to separate, even after affinity purification.

The frequency of appearance of the second form in various intact IgG isotypes is due to, but not limited to, structural differences associated with the hinge region isotype of the antibody. A single amino acid substitution in the hinge region of the human IgG4 hinge can significantly reduce the appearance of the second form to levels typically observed using a human IgG1 hinge. The instant disclosure encompasses in various embodiments antibodies having one or more mutations in the hinge, CH2 or CH3 region which may be desirable, for example, in production, to improve the yield of the desired antibody form.

An "isolated antibody," as used herein, means an antibody that has been identified and separated and/or recovered from at least one component of its natural environment. For example, an antibody that has been separated or removed from at least one component of an organism, or from a tissue or cell in which the antibody naturally exists or is naturally produced, is an "isolated antibody." In various embodiments, the isolated antibody also includes an antibody in situ within a recombinant cell. In other embodiments, isolated antibodies are antibodies that have been subjected to at least one purification or isolation step. In various embodiments, an isolated antibody may be substantially free of other cellular material and/or chemicals.

The term "specifically binds," or the like, means that an antibody or antigen-binding fragment thereof forms a complex with an antigen that is relatively stable under physiologic conditions. Methods for determining whether an antibody specifically binds to an antigen are well known in the art and include, for example, equilibrium dialysis, surface plasmon resonance, and the like. For example, an antibody that "specifically binds" IL-6R, as used herein, includes antibodies that bind IL-6R (e.g., human IL-6R) or portion thereof with a KD of less than about 1000 nM, less than about 500 nM, less than about 300 nM, less than about 200 nM, less than about 100 nM, less than about 90 nM, less than about 80 nM, less than about 70 nM, less than about 60 nM, less than about 50 nM, less than about 40 nM, less than about 30 nM, less than about 20 nM, less than about 10 nM, less than about 5 nM, less than about 4 nM, less than about 3 nM, less than about 2 nM, less than about 1 nM or about 0.5 nM, as measured in a surface plasmon resonance assay. In some embodiments, the antibody binds IL-6R (e.g., human IL-6Rα) with a KD of from about 0.1 nM to about 1000 nM or from about 1 nM to about 100 nM. In some embodiments, the antibody binds IL-6R (e.g., human IL-6Rα) with a KD of from about 1 pM to about 100 pM or from about 40 pM to about 60 pM. Specific binding can also be characterized by a dissociation constant of at least about $1\times10^{-6}$ M or smaller. In other embodiments, the dissociation constant is at least about $1\times10^{-7}$ M, $1\times10^{-8}$ M, or $1\times10^{-9}$ M. An isolated antibody that specifically binds human IL-6R may, however, have cross-reactivity to other antigens, such as IL-6R molecules from other (non-human) species.

The term "surface plasmon resonance," as used herein, refers to an optical phenomenon that allows for the analysis of real-time interactions by detection of alterations in protein concentrations within a biosensor matrix, for example using the BIACORE® system (Biacore Life Sciences division of GE Healthcare, Piscataway, NJ).

The term "KD," as used herein, is intended to refer to the equilibrium dissociation constant of an antibody-antigen interaction.

The term "epitope" refers to an antigenic determinant that interacts with a specific antigen binding site in the variable region of an antibody molecule known as a paratope. A single antigen may have more than one epitope. Thus, different antibodies may bind to different areas on an antigen and may have different biological effects. Epitopes may be either conformational or linear. A conformational epitope is produced by spatially juxtaposed amino acids from different segments of the linear polypeptide chain. A linear epitope is one produced by adjacent amino acid residues in a polypeptide chain. In certain circumstance, an epitope may include moieties of saccharides, phosphoryl groups, or sulfonyl groups on the antigen.

The anti-IL-6R antibodies useful for the methods described herein may in various embodiments include one or more amino acid substitutions, insertions and/or deletions in the framework and/or CDR regions of the heavy and light chain variable domains as compared to the corresponding germline sequences from which the antibodies were derived. Such mutations can be readily ascertained by comparing the amino acid sequences disclosed herein to germline sequences available from, for example, public antibody sequence databases. The present disclosure includes in various embodiments methods involving the use of antibodies, and antigen-binding fragments thereof, which are derived from any of the amino acid sequences disclosed herein, wherein one or more amino acids within one or more framework and/or CDR regions are mutated to the corresponding residue(s) of the germline sequence from which the antibody was derived, or to the corresponding residue(s) of another human germline sequence, or to a conservative amino acid substitution of the corresponding germline residue(s) (such sequence changes are referred to herein collectively as "germline mutations"). Numerous antibodies and antigen-binding fragments may be constructed which comprise one or more individual germline mutations or combinations thereof. In certain embodiments, all of the framework and/or CDR residues within the VH and/or VL domains are mutated back to the residues found in the original germline sequence from which the antibody was derived. In other embodiments, only certain residues are mutated back to the original germline sequence, e.g., only the mutated residues found within the first 8 amino acids of FR1 or within the last 8 amino acids of FR4, or only the mutated residues found within CDR1, CDR2 or CDR3. In other embodiments, one or more of the framework and/or CDR residue(s) are mutated to the corresponding residue(s) of a different germline sequence (i.e., a germline sequence that is different from the germline sequence from which the antibody was originally derived). Furthermore, the antibodies may contain any combination of two or more germline mutations within the framework and/or CDR regions, e.g., wherein certain individual residues are mutated to the corresponding residue of a certain germline sequence while certain other residues that differ from the original germline sequence are maintained or are mutated to the corresponding residue of a different germline sequence. Once obtained, antibodies and antigen-binding fragments that contain one or more germline mutations can be easily tested for one or more desired property such as, improved binding specificity, increased binding affinity, improved or enhanced antagonistic or agonistic biological properties (as the case may be), reduced immunogenicity, etc. The use of antibodies and antigen-binding fragments obtained in this general manner are encompassed within the present disclosure.

The present disclosure also includes methods involving the use of anti-IL-6R antibodies comprising variants of any of the HCVR, LCVR, and/or CDR amino acid sequences disclosed herein having one or more conservative substitutions. For example, the present disclosure includes the use of anti-IL-6R antibodies having HCVR, LCVR, and/or CDR amino acid sequences with, e.g., 10 or fewer, 8 or fewer, 6 or fewer, 4 or fewer, etc. conservative amino acid substitutions relative to any of the HCVR, LCVR, and/or CDR amino acid sequences disclosed herein.

According to the present disclosure, the anti-IL-6R antibody, or antigen-binding fragment thereof, in various embodiments comprises a heavy chain variable region (HCVR), light chain variable region (LCVR), and/or complementarity determining regions (CDRs) comprising any of the amino acid sequences of the anti-IL-6R antibodies described in U.S. Pat. No. 7,582,298, incorporated herein by reference in its entirety. In certain embodiments, the anti-IL-6R antibody or antigen-binding fragment thereof comprises the heavy chain complementarity determining regions (HCDRs) of a HCVR comprising the amino acid sequence of SEQ ID NO: 1 and the light chain complementarity determining regions (LCDRs) of a LCVR comprising the amino acid sequence of SEQ ID NO: 2. According to certain embodiments, the anti-IL-6R antibody or antigen-binding fragment thereof comprises three HCDRs (i.e., HCDR1, HCDR2 and HCDR3) and three LCDRs (i.e., LCDR1, LCDR2 and LCDR3), wherein the HCDR1 comprises the amino acid sequence of SEQ ID NO: 3; the HCDR2 comprises the amino acid sequence of SEQ ID NO: 4; the HCDR3 comprises the amino acid sequence of SEQ ID NO: 5; the LCDR1 comprises the amino acid sequence of SEQ ID NO: 6; the LCDR2 comprises the amino acid sequence of SEQ ID NO: 7; and the LCDR3 comprises the amino acid sequence of SEQ ID NO: 8. In yet other embodiments, the anti-IL-6R antibody or antigen-binding fragment thereof comprises an HCVR comprising the amino acid sequence of SEQ ID NO: 1 and an LCVR comprising the amino acid sequence of SEQ ID NO: 2.

In another embodiment, the anti-IL-6R antibody or antigen-binding fragment thereof comprises a heavy chain comprising the amino acid sequence of SEQ ID NO: 9 and a light chain comprising the amino acid sequence of SEQ ID NO: 10. In some embodiments, the extracellular domain of hIL-6R comprises the amino acid sequence of SEQ ID NO: 11. According to certain exemplary embodiments, the methods of the present disclosure comprise the use of the anti-IL-6R antibody referred to and known in the art as sarilumab, or a bioequivalent thereof.

The amino acid sequence of SEQ ID NO: 1 is

EVQLVESGGGLVQPGRSLRLSCAASRFTFDDYAMHWVRQAPGKGLEWVS

GISWNSGRIGYADSVKGRFTISRDNAENSLFLQMNGLRAEDTALYYCAK

GRDSFDIWGQGTMVTVSS.

The amino acid sequence of SEQ ID NO: 2 is

DIQMTQSPSSVSASVGDRVTITCRASQGISSWLAWYQQKPGKAPKLLIY

GASSLESGVPSRFSGSGSGTDFTLTISSLQPEDFASYYCQQANSFPYTF

GQGTKLEIK.

The amino acid sequence of SEQ ID NO: 3 is RFTFDDYA.

The amino acid sequence of SEQ ID NO: 4 is ISWNSGRI.

The amino acid sequence of SEQ ID NO: 5 is AKGRDSFDI.

The amino acid sequence of SEQ ID NO: 6 is QGISSW.

The amino acid sequence of SEQ ID NO: 7 is GAS.

The amino acid sequence of SEQ ID NO: 8 is QQANSFPYT.

The amino acid sequence of SEQ ID NO: 9 is

EVQLVESGGGLVQPGRSLRLSCAASRFTFDDYAMHWVRQAPGKGLEWVS

GISWNSGRIGYADSVKGRFTISRDNAENSLFLQMNGLRAEDTALYYCAK

GRDSFDIWGQGTMVTVSSASTKGPSVFPLAPSSKSTSGGTAALGCLVKD

YFPEPVTVSWNSGALTSGVHTFPAVLQSSGLYSLSSVVTVPSSSLGTQT

YICNVNHKPSNTKVDKKVEPKSCDKTHTCPPCPAPELLGGPSVFLFPPK

PKDTLMISRTPEVTCVVVDVSHEDPEVKFNWYVDGVEVHNAKTKPREEQ

YNSTYRVVSVLTVLHQDWLNGKEYKCKVSNKALPAPIEKTISKAKGQPR

EPQVYTLPPSRDELTKNQVSLTCLVKGFYPSDIAVEWESNGQPENNYKT

TPPVLDSDGSFFLYSKLTVDKSRWQQGNVFSCSVMHEALHNHYTQKSLS

LSPGK.

The amino acid sequence of SEQ ID NO: 10 is

DIQMTQSPSSVSASVGDRVTITCRASQGISSWLAWYQQKPGKAPKLLIY

GASSLESGVPSRFSGSGSGTDFTLTISSLQPEDFASYYCQQANSFPYTF

GQGTKLEIKRTVAAPSVFIFPPSDEQLKSGTASVVCLLNNFYPREAKVQ

WKVDNALQSGNSQESVTEQDSKDSTYSLSSTLTLSKADYEKHKVYACEV

THQGLSSPVTKSFNRGEC.

The sequence of SEQ ID NO: 11 is

MVAVGCALLAALLAAPGAALAPRRCPAQEVARGVLTSLPGDSVTLTCPG

VEPEDNATVHWVLRKPAAGSHPSRWAGMGRRLLLRSVQLHDSGNYSCYR

AGRPAGTVHLLVDVPPEEPQLSCFRKSPLSNVVCEWGPRSTPSLTTKAV

LLVRKFQNSPAEDFQEPCQYSQESQKFSCQLAVPEGDSSFYIVSMCVAS

SVGSKFSKTQTFQGCGILQPDPPANITVTAVARNPRWLSVTWQDPHSWN

-continued

```
SSFYRLRFELRYRAERSKTFTTWMVKDLQHHCVIHDAWSGLRHVVQLRA

QEEFGQGEWSEWSPEAMGTPWTESRSPPAENEVSTPMQALTTNKDDDNI

LFRDSANATSLPVQD.
```

The term "bioequivalent" as used herein, refers to a molecule having similar bioavailability (rate and extent of availability) after administration at the same molar dose and under similar conditions (e.g., same route of administration), such that the effect, with respect to both efficacy and safety, can be expected to be essentially same as the comparator molecule. Two pharmaceutical compositions comprising an anti-IL-6R antibody are bioequivalent if they are pharmaceutically equivalent, meaning they contain the same amount of active ingredient (e.g., IL-6R antibody), in the same dosage form, for the same route of administration and meeting the same or comparable standards. Bioequivalence can be determined, for example, by an in vivo study comparing a pharmacokinetic parameter for the two compositions. Parameters commonly used in bioequivalence studies include peak plasma concentration (Cmax) and area under the plasma drug concentration time curve (AUC).

The disclosure in certain embodiments relates to methods comprising administering to the subject an antibody which comprises the heavy chain variable region comprising sequence SEQ ID NO: 1 and the light chain variable region comprising sequence SEQ ID NO: 2.

The disclosure provides pharmaceutical compositions comprising such antibody, and methods of using these compositions.

The antibody in various embodiments comprises the heavy chain variable region comprising sequence SEQ ID NO: 1 and the light chain variable region comprising sequence SEQ ID NO: 2 is an antibody that specifically binds human interleukin-6 receptor (hIL-6R). See international publication number WO2007/143168, incorporated herein by reference in its entirety. In one embodiment, the antibody comprises the heavy chain variable region comprising sequence SEQ ID NO: 9 and the light chain variable region comprising sequence SEQ ID NO: 10. In various embodiments, the antibody is sarilumab.

DMARDs

Disease-modifying antirheumatic drugs (DMARDs) are drugs defined by their use in rheumatoid arthritis to slow down disease progression. DMARDs have been classified as synthetic (sDMARD) and biological (bDMARD). Synthetic DMARDs include non-exhaustively methotrexate, sulfasalazine, leflunomide, and hydroxychloroquine. Biological DMARDs include non-exhaustively adalimumab, golimumab, etanercept, abatacept, infliximab, rituximab, and tocilizumab. In some embodiments, the DMARD is a TNF antagonist. TNF antagonists include, but are not limited to, etanercept, infliximab, adalimumab, golimumab and certolizumab pegol.

Methods of Administration and Formulations

The methods described herein comprise administering a therapeutically effective amount of an anti-IL-6R antibody to a subject. As used herein, an "effective amount" or "therapeutically effective amount" is a dose of the therapeutic that results in treatment of NIP. In certain embodiments, effective amount is a dose of the therapeutic that results in treatment of NIP that persists despite inflammation control (IC). As used herein, "treating" refers to causing a detectable improvement in one or more symptoms associated with NIP or causing a biological effect (e.g., a decrease in the level of a particular biomarker) that is correlated with the underlying pathologic mechanism(s) giving rise to the condition or symptom(s). For example, a dose of anti-IL-6R antibody which causes a reduction in NIP is deemed a "therapeutically effective amount."

An "improvement" in an NIP-associated symptom in various embodiments refers reduction in the incidence of the pain symptom which may correlate with an improvement in one or more pain-associated tests, scores or metrics (as described herein). For example, the improvement may correlate a decrease from baseline of one or more of pain criteria. In various embodiments, improvement may comprise a decrease in VAS from baseline. As used herein, the term "baseline," with regard to a pain-associated parameter, means the numerical value of the pain-associated parameter for a patient prior to or at the time of administration of the antibody of the present technology. A detectable "improvement" can also be detected using at least one test, score or metric described herein. In various embodiments, the improvement is detected using VAS. In various embodiments, the improvement is characterized by its relation to a subject's PASS status.

In various embodiments, previous treatment with a DMARD other than an anti-IL-6R antibody (such as sarilumab) has been inadequate (e.g., as assessed by the subject and/or a physician), has been ineffective and/or has not resulted in a detectable improvement in one or more parameters or symptoms associated with NIP and/or has not caused a biological effect that is correlated with the underlying pathologic mechanism(s) giving rise to the condition or symptom(s) of NIP.

In various embodiments, a IL-6R antibody is administered subcutaneously. In various embodiments, the IL-6R antibody is sarilumab.

In various embodiments, a therapeutically effective amount of anti-IL-6R antibody that is administered to the subject will vary depending upon the age and the size (e.g., body weight or body surface area) of the subject as well as the route of administration and other factors well known to those of ordinary skill in the art.

In various embodiments, the dose is a fixed dose regardless of the body weight or surface area of the subject. In various embodiments, the subject is at least 18 years old. In various embodiments, the subject is from 30 to 100 years old. In various embodiments, the subject is from 35 to 100 years old. In various embodiments, the subject is from 35 to 8 years old. In various embodiments, the subject is from 40 to 70 years old.

The disclosure provides methods of using therapeutic compositions comprising anti-IL-6R antibodies or antigen-binding fragments thereof and, optionally, one or more additional therapeutic agents. The therapeutic compositions of the present disclosure will be administered with suitable carriers, excipients, and/or other agents that are incorporated into formulations to provide improved transfer, delivery, tolerance, and the like. A multitude of appropriate formulations can be found in the formulary known to all pharmaceutical chemists: Remington's Pharmaceutical Sciences, Mack Publishing Company, Easton, PA. These formulations include, for example, powders, pastes, ointments, jellies, waxes, oils, lipids, lipid (cationic or anionic) containing vesicles (such as LIPOFECTIN®), DNA conjugates, anhydrous absorption pastes, oil-in-water and water-in-oil emulsions, emulsions carbowax (polyethylene glycols of various molecular weights), semi-solid gels, and semi-solid mixtures containing carbowax.

Various delivery systems are known and can be used to administer pharmaceutical compositions provided herein, e.g., encapsulation in liposomes, microparticles, microcapsules, receptor mediated endocytosis. Methods of introduction include, but are not limited to, intradermal, intramuscular, intraperitoneal, intravenous, subcutaneous, intranasal, epidural, and oral routes. The composition may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. The IL-6R antibody can be administered subcutaneously.

The pharmaceutical composition can also be delivered in a vesicle, such as a liposome In certain embodiments, the pharmaceutical composition can be delivered in a controlled release system, for example, with the use of a pump or polymeric materials. In certain embodiments, a controlled release system can be placed in proximity of the composition's target, thus requiring only a fraction of the systemic dose.

The injectable preparations may include dosage forms for intravenous, subcutaneous, intracutaneous and intramuscular injections, local injection, drip infusions, etc. These injectable preparations may be prepared by methods publicly known. For example, the injectable preparations may be prepared, e.g., by dissolving, suspending or emulsifying the antibody or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc.). As the oily medium, there are employed, e.g., sesame oil, soybean oil, etc., which may be used in combination with a solubilizing agent such as benzyl benzoate, benzyl alcohol, etc. The injection thus prepared can be filled in an appropriate ampoule.

The antibody is typically formulated as described herein and in international publication number WO2011/085158, incorporated herein by reference in its entirety.

In various embodiments, the antibody is administered as an aqueous buffered solution at about pH 6.0 containing about 21 mM histidine,
about 45 mM arginine,
about 0.2% (w/v) polysorbate 20,
about 5% (w/v) sucrose, and
between about 100 mg/mL and about 200 mg/mL of the antibody.

In another embodiment, the antibody is administered as an aqueous buffered solution at about pH 6.0 containing about 21 mM histidine,
about 45 mM arginine,
about 0.2% (w/v) polysorbate 20,
about 5% (w/v) sucrose, and
at least about 130 mg/mL of the antibody.

In another embodiment, the antibody is administered as an aqueous buffered solution at about pH 6.0 containing about 21 mM histidine,
about 45 mM arginine,
about 0.2% (w/v) polysorbate 20,
about 5% (w/v) sucrose, and
about 131.6 mg/mL of the antibody.

In another embodiment, the antibody is administered as an aqueous buffered solution at about pH 6.0 containing about 21 mM histidine,
about 45 mM arginine,
about 0.2% (w/v) polysorbate 20,
about 5% (w/v) sucrose; and
about 175 mg/mL of the antibody.

In other embodiments, the antibody is administered as an aqueous buffered solution at pH 6.0 containing 21 mM histidine,
45 mM arginine,
0.2% (w/v) polysorbate 20,
5% (w/v) sucrose, and
between 100 mg/mL and 200 mg/mL of the antibody.

In another embodiment, the antibody is administered as an aqueous buffered solution at pH 6.0 containing 21 mM histidine,
45 mM arginine,
0.2% (w/v) polysorbate 20,
5% (w/v) sucrose, and
at least 130 mg/mL of the antibody.

In another embodiment, the antibody is administered as an aqueous buffered solution at pH 6.0 containing 21 mM histidine,
45 mM arginine,
0.2% (w/v) polysorbate 20,
5% (w/v) sucrose, and
131.6 mg/mL of the antibody.

In another embodiment, the antibody is administered as an aqueous buffered solution at pH 6.0 containing 21 mM histidine,
45 mM arginine,
0.2% (w/v) polysorbate 20,
5% (w/v) sucrose; and
175 mg/mL of the antibody.

In various embodiments, the antibody is administered in a stable pharmaceutical formulation comprising: (i) histidine at a concentration of from 25 mM to 100 mM; (ii) arginine at a concentration of from 25 mM to 50 mM; (iii) sucrose in an amount of from 3% to 10% w/v; and (iv) polysorbate 20 in an amount of from 0.1% to 0.2%, wherein the formulation has a pH of about 5.8, about 6.0, or about 6.2, and at least 90% of the native form of the antibody is recovered after 1 month of storage at 45° C., as determined by size exclusion chromatography. In various embodiments, about 150 mg of the antibody (e.g., sarilumab) is administered to the subject.

In various embodiments, the antibody is administered in a stable pharmaceutical formulation comprising: (i) histidine at a concentration of from about 10 mM to about 25 mM; (ii) arginine at a concentration of from about 25 mM to about 50 mM; (iii) sucrose in an amount of from about 5% to about 10% w/v; and (iv) polysorbate in an amount of from about 0.1% to about 0.2% w/v, wherein the formulation has a pH of about 5.8, about 6.0, or about 6.2, and at least 90% of the native form of the antibody is recovered after 1 month of storage at 45° C., as determined by size exclusion chromatography. In various embodiments, about 150 mg of the antibody (e.g., sarilumab) is administered to the subject.

Advantageously, the pharmaceutical compositions for oral or parenteral use described above are prepared into dosage forms in a unit dose suited to fit a dose of the active ingredients. Such dosage forms in a unit dose include, for example, tablets, pills, capsules, injections (ampoules), suppositories, etc.

In various embodiments, the anti-IL-6R antibody (or pharmaceutical formulation comprising the antibody) can be administered to the patient using any acceptable device or mechanism. For example, the administration can be accomplished using a syringe and needle or with a reusable pen and/or autoinjector delivery device. The methods of the present disclosure include the use of numerous reusable pen and/or autoinjector delivery devices to administer an anti-IL-6R antibody (or pharmaceutical formulation comprising the antibody). Examples of such devices include, but are not limited to AUTOPEN® (Owen Mumford, Inc., Woodstock, UK), DISETRONIC® pen (Disetronic Medical Systems, Bergdorf, Switzerland), HUMALOG MIX® 75/25 pen, HUMALOG® pen, HUMALIN® 70/30 pen (Eli Lilly and Co., Indianapolis, IN), NOVOPEN® I, II and III (Novo Nordisk, Copenhagen, Denmark), NOVOPEN JUNIOR® (Novo Nordisk, Copenhagen, Denmark), BD® pen (Becton Dickinson, Franklin Lakes, NJ), OPTIPEN®, OPTIPEN PRO®, OPTIPEN STARLET®, and OPTICLIK® (Sanofi-Aventis, Frankfurt, Germany). Examples of disposable pen and/or autoinjector delivery devices having applications in subcutaneous delivery of a pharmaceutical composition of the present disclosure include, but are not limited to the SOLOSTAR® pen (Sanofi-Aventis), the FLEXPEN® (Novo Nordisk), and the KWIKPEN® (Eli Lilly), the SURECLICK® Autoinjector (Amgen, Thousand Oaks, CA), the PENLET® (Haselmeier, Stuttgart, Germany), the EPIPEN® (Dey, L. P.), and the HUMIRA® Pen (AbbVie Inc., North Chicago, IL), to name only a few.

In various embodiments, the antibody is administered with a prefilled syringe. In various embodiments, the antibody is administered with a prefilled syringe containing a safety system. For example, the safety system prevents an accidental needle-stick injury. In various embodiments, the antibody is administered with a prefilled syringe containing an ERIS safety system (West Pharmaceutical Services Inc.).

In various embodiments, the antibody is administered with an auto-injector. In various embodiments, the antibody is administered with an auto-injector featuring the PUSHCLICK® technology (SHL Group). In various embodiments, the auto-injector is a device comprising a syringe that allows for administration of a dose of the composition and/or antibody to a subject.

The use of a microinfusor to deliver an anti-IL-6R antibody (or pharmaceutical formulation comprising the antibody) to a patient is also contemplated herein. As used herein, the term "microinfusor" means a subcutaneous delivery device designed to slowly administer large volumes (e.g., up to about 2.5 mL or more) of a therapeutic formulation over a prolonged period of time (e.g., about 10, 15, 20, 25, 30 or more minutes). Microinfusors are particularly useful for the delivery of large doses of therapeutic proteins contained within high concentration (e.g., about 100, 125, 150, 175, 200 mg/mL or more) and/or viscous solutions.

In various embodiments, an inadequate response to prior treatment refers to subjects whose pain is not well controlled after receiving the prior treatment at the maximum tolerated typical dose. In an embodiment, an inadequate response to prior treatment refers to subjects who have moderate or high disease activity and features of poor prognosis despite prior treatment. In various embodiments, an inadequate response to prior treatment refers to subjects with a pain symptom (e.g., any symptom listed herein) that has not improved or that has worsened despite prior treatment.

Patient Population

As used herein, "subject" means a human subject or human patient.

An antibody as described herein is in various embodiments administered to subjects who have rheumatoid arthritis and are suffering from NIP. In various embodiments, the subject has NIP and rheumatoid arthritis. In various embodiments, the subject was previously ineffectively treated for rheumatoid arthritis by administering one or more DMARDs different from the IL-6R antibody.

A subject who is considered "ineffectively treated" by his or her physician is a subject who in various embodiments either has shown to be intolerant to the one or more DMARDs tested by the physician, and/or a subject who has shown an inadequate response to the one or more DMARDs tested by the physician, typically a subject who is still considered by the physician to present with, or to have, NIP despite the previous one or more DMARDs administered.

In various embodiments, a subject with rheumatoid arthritis has:

at least 6 of 66 swollen joints and 8 of 68 tender joints, as counted by the physician in a typical quantitative swollen and tender joint count examination, High sensitivity C-reactive protein (hs-CRP)≥8 mg/L or ESR≥28 mm/H

DAS28ESR>5.1.

In various embodiments, the subject, who was previously ineffectively treated for rheumatoid arthritis by administering at least one DMARD different from the antibody, is a subject who was previously ineffectively treated for NIP by administering a DMARD. In various embodiments, the DMARD is selected from the group consisting of methotrexate, sulfasalazine, leflunomide, and hydroxychloroquine. In various embodiments, the DMARD is methotrexate. In various embodiments, the DMARD is a TNF-α antagonist. In various embodiments, the DMARD is adalimumab.

In various embodiments, the subject, who was previously ineffectively treated for NIP by administering one or more DMARDs different from the antibody, is a subject who had an inadequate response or intolerance to methotrexate.

In various embodiments, the subject, who was previously ineffectively treated for NIP by administering one or more DMARDs different from the antibody, is a subject who had an inadequate response or intolerance to adalimumab.

In various embodiments, for those subjects previously ineffectively treated for NIP by administering one or more DMARDs different from the IL-6R antibody, the one or more DMARDs is/are not administered anymore to the subject, and the IL-6R antibody is in various embodiments administered alone, in monotherapy to the subject.

In various embodiments, the subject is intolerant to the DMARD due to one or more physical reactions, conditions or symptoms from the treatment with the DMARD. Physical reactions, conditions or symptoms can include allergies, pain, nausea, diarrhea, azotemia, bleeding of the stomach, intestinal bleeding, canker sores, decreased blood platelets, perforation of the intestine, bacterial infection, inflammation of gums or mouth, inflammation of the stomach lining or intestinal lining, bacterial sepsis, stomach ulcer, intestinal ulcer, sun sensitive skin, dizziness, loss of appetite, low energy, and vomiting. In certain embodiments, intolerance can be determined by the subject or by a medical professional upon examination of the subject. In various embodiments, the DMARD is selected from the group consisting of methotrexate, sulfasalazine, leflunomide, and hydroxychloroquine. In certain embodiments, the DMARD is methotrexate. In certain embodiments, the DMARD is adalimumab.

In certain embodiments the disclosure provides administering to the subject one or more additional therapeutic agents in combination with the IL-6R antibody. As used herein, the expression "in combination with" means that the additional therapeutic agents are administered before, after, or concurrent with the pharmaceutical composition comprising the IL-6R antibody. In certain embodiments, the subject is administered the antibody with a DMARD and/or TNF-α antagonist.

EXAMPLE

Example 1: Sarilumab, NIP Status and Disease Activity

In the present study, the prevalence of non-inflammatory pain (NIP), the effect of sarilumab on NIP, and the association between sarilumab treatment, disease activity, and NIP status at baseline was investigated and then again after 3 and 6 months of sarilumab treatment.

Data Sources

Patient data were pooled from two placebo-controlled RCTs of sarilumab 150 mg and 200 mg q2w (MOBILITY, NCT01061736; TARGET, NCT01709578), and one adalimumab-controlled RCT of sarilumab 200 mg q2w (MONARCH, NCT02332590).

Study Endpoints

NIP was defined as a difference between the 28-joint tender joint count (TJC) and swollen joint count (SJC), using the established formula: TJC−SJC≥7[10,11] Patients were assessed for NIP at study baseline and for change in NIP status at weeks 12 and 24. Finally, proportions of patients achieving American College of Rheumatology 20/50/70 (ACR20/50/70) criteria, Clinical Disease Activity Index (CDAI)≤10, and 28-joint Disease Activity Score with C-reactive protein (DAS28-CRP)<3.2 at week 24 were assessed in patients with and without baseline NIP.

Results

Demographic and Baseline Disease Characteristics by NIP Status

Patients with baseline NIP had higher composite measures of disease activity versus patients without NIP, although measures of inflammation were similar (Table 1). Of the 2112 patients who were included in the analysis, 490 (23%) had NIP at baseline (MOBILITY, 25% [294/1197]; TARGET, 19% [106/546]; MONARCH, 24% [90/369]). Patients with and without baseline NIP had similar demographic characteristics at baseline (Table 2).

TABLE 1

Baseline Disease Characteristics by NIP status
Baseline Disease Characteristics by NIP Status: Pooled MOBILITY,[7] TARGET,[8] and MONARCH[9] Data

| | With NIP (n = 490) | Without NIP (n = 1622) |
|---|---|---|
| Duration of RA, years | 9.1 ± 8.6 | 9.7 ± 8.4 |
| TJC (range 0-28) | 21.7 ± 4.7 | 14.3 ± 6.2 |
| SJC (range 0-28) | 10.7 ± 4.3 | 13.1 ± 6.0 |
| CRP, mg/L | 22.7 ± 27.0 | 22.9 ± 24.0 |
| HAQ-DI (range 0-3) | 1.8 ± 0.6 | 1.7 ± 0.6 |
| DAS28-CRP | 6.4 ± 0.7 | 5.9 ± 0.9 |
| CDAI | 46.0 ± 9.4 | 40.4 ± 13.0 |
| Pain VAS (range 0-100) | 72 ± 18 | 67 ± 21 |

All values mean ± SD;
HAQ-DI = Health Assessment Questionnaire-Disability Index;
VAS = visual analog scale

TABLE 2

Baseline Demographics by NIP status

| Parameter | With NIP (n = 490) | Without NIP (n = 1622) |
|---|---|---|
| Age, mean ± SD, years | 53 ± 11 | 51 ± 12 |
| Women, n (%) | 415 (85) | 1316 (81) |
| Race, n (%) | | |
| White | 416 (85) | 1338 (82) |
| Black | 12 (2) | 40 (2) |
| Asian | 24 (5) | 90 (6) |
| Other | 38 (8) | 154 (9) |
| Hispanic ethnicity, n (%) | 160 (33) | 612 (38) |
| Weight, mean ± SD, kg | 75 ± 19 | 75 ± 19 |
| BMI group, n (%) | | |
| <25 kg/m$^2$ | 151 (31) | 546 (35) |
| ≥25 kg/m$^2$ and <30 kg/m$^2$ | 172 (35) | 550 (34) |
| ≥30 kg/m$^2$ | 166 (34) | 520 (32) |
| Opioid use, n (%) | 57 (12) | 214 (13) |

Sarilumab, NIP Status, and Disease Activity

Figure 2:
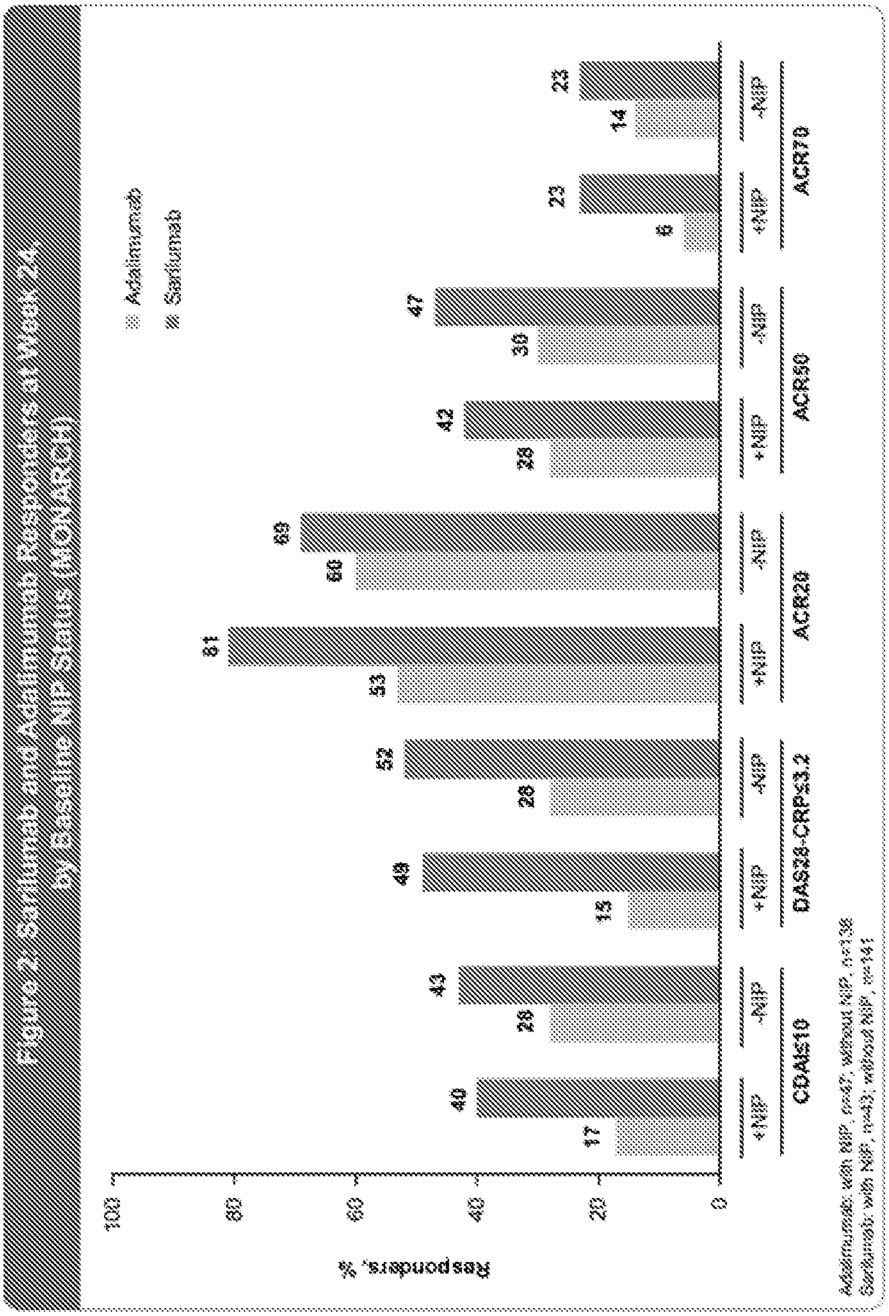
FIG. 2 shows NIP status of sarilumab or adalimumab responders at week 24.

Among patients with baseline NIP, those who received sarilumab were more likely to have no NIP at weeks 12 and 24 versus patients who received placebo or adalimumab (FIG. 1). In all three studies (MOBILITY, TARGET and MONARCH), the relative difference between sarilumab and control treatments appeared to increase with treatment duration. In MONARCH, a higher proportion of sarilumab- than adalimumab-treated patients achieved therapeutic response at week 24, regardless of the presence of baseline NIP (FIG. 2). The relative differences between treatment groups were larger among patients with baseline NIP for all assessments except ACR50. After 3 and 6 months of treatment, there was a greater prevalence of noninflammatory pain in patients treated with placebo and adalimumab, compared with patients treated with sarilumab. Further, regardless of non-inflammatory pain at baseline, a higher proportion of patients achieved low disease activity with sarilumab than adalimumab after 6 months of treatment.

CONCLUSION

At weeks 12 and 24, NIP was less prevalent in patients treated with sarilumab than in patients treated with placebo or adalimumab. This data shows that NIP contributes to pain in RA patients, and that NIP in RA patients can be treated with composition in the present disclosure.

REFERENCES

1. Boyden S D, et al. *Curr Rheumatol Rep* 2016; 18:30.
2. Choy E H S, Calabrese L H. *Rheumatology* (*Oxford*) 2018; 57:1885-95.
3. Brenn D, et al. *Arthritis Rheum* 2007; 56:351-9.
4. Zhou Y Q, et al. *J Neuroinflammation* 2016; 13:141.
5. KEVZARA (sarilumab) [Summary of Product Characteristics]. Bridgewater, NJ: Sanofi.
6. KEVZARA (sarilumab) [Prescribing Information] 2017. Bridgewater, NJ: Sanofi.
7. Strand V, et al. *Arthritis Res Ther* 2016; 18:198.
8. Strand V, et al. *RMD Open* 2017; 3:e000416.
9. Burmester G R, et al. *Ann Rheum Dis* 2017; 76:840-7.
10. Duran J, et al. *Rheumatology* (*Oxford*) 2015; 54:2166-70.
11. Pollard L C, et al. *Rheumatology* (*Oxford*) 2010; 49:924-8.

12. Schaible H. Nociceptive neurons detect cytokines in arthritis. Arthritis Res Ther. 2014; 16(5):470.
13. Turk D, Okifuji A. Pain terms and taxonomies. Bonica's Management of Pain. 3rd ed: Lippincott Williams & Wilkins; 2001.
14. Yang S, Chang M. Chronic pain: Structural and functional changes in brain structures and associated negative affective states. Int J Mol Sci. 2019; 20(13):3130.
15. Schaible H. Nociceptive neurons detect cytokines in arthritis. Arthritis Res Ther. 2014; 16(5): 470.
16. Cazzola M, et al. Physiopathology of pain in rheumatology. Reumatismo. 2014; 66(1):4-13.
17. Deane K D, et al. Preclinical rheumatoid arthritis: identification, evaluation, and future directions for investigation. Rheum Dis Clin North Am. 2010; 36(2):213-41.
18. de Haas W H, et al. Rheumatoid arthritis, typus robustus. Ann Rheum Dis. 1973; 32(1):91-2.
19. Kristensen L E, et al. Is swollen to tender joint count ratio a new and useful clinical marker for biologic drug response in rheumatoid arthritis? results from a Swedish cohort. Arthritis Care Res (Hoboken). 2014; 66(2):173-9
20. Challa D N, et al. Patient-provider discordance between global assessments of disease activity in rheumatoid arthritis: A comprehensive clinical evaluation. Arthritis Res Ther. 2017; 19(1):212.
21. Khan N A, et al. Determinants of discordance in patients' and physicians' rating of rheumatoid arthritis disease activity. Arthritis Care Res (Hoboken). 2012; 64(2):206-14.
22. Studenic P, et al. Discrepancies between patients and physicians in their perceptions of rheumatoid arthritis disease activity. Arthritis Rheum. 2012; 64(9):2814-23.
23. Hammer H, et al. Major reduction of ultrasound detected synovitis during subcutaneous tocilizumab treatment; results from a multicenter 24 weeks study of patients with rheumatoid arthritis [abstract]. Arthritis Rheumatol. 2018; 70(suppl 10).
24. Maini R S C, E. W., et al. Infliximab (chimeric anti-tumour necrosis factor alpha monoclonal antibody) versus placebo in rheumatoid arthritis patients receiving concomitant methotrexate: A randomised phase III trial. ATTRACT study group. Lancet. 1999; 354(9194): 1932-9.
25. Lee Y C, et al. Pain persists in DAS28 rheumatoid arthritis remission but not in ACR/EULAR remission: A longitudinal observational study. Arthritis Res Ther. 2011; 13(3):R83.
26. Taylor P, et al. Patient perceptions concerning pain management in the treatment of rheumatoid arthritis. J Int Med Res. 2010; 38(4):1213-24.
27. Sarzi-Puttini P, et al. Correlation of the score for subjective pain with physical disability, clinical and radiographic scores in recent onset rheumatoid arthritis. BMC Musculoskelet Disord. 2002; 3:18.
28. McWilliams D F, Walsh D A. Pain mechanisms in rheumatoid arthritis. Clin Exp Rheumatol. 2017; 35(5): 94-101.
29. Flodin P, et al. Intrinsic brain connectivity in chronic pain: A resting-state fMRI study in patients with rheumatoid arthritis. Front Hum Neurosci. 2016; 10:107.
30. Biswas M, et al. Prevalence, types, clinical associations, and determinants of peripheral neuropathy in rheumatoid patients. Ann Indian Acad Neurol. 2011; 14(3):194-7.
31. Adlan A, et al. Autonomic function and rheumatoid arthritis: A systematic review. Semin Arthritis Rheum 2014; 44(3):283-304.
32. Walsh D A, McWilliams D F. Mechanisms, impact and management of pain in rheumatoid arthritis. Nat Rev Rheumatol. 2014; 10(10):581-92.
33. Ramachandran V S, Blakeslee S. Phantoms in the brain: human nature and the architecture of the mind: Harper-Collins; 1998.
34. Taylor et al., Nucl. Acids Res. 1992; 20:6287-6295.
35. Angal et al., Molecular Immunology; 1993 30:105.
36. Powell et al. "Compendium of excipients for parenteral formulations" PDA J Pharm Sci Technol 1998; 52:238-311.
37. Wu et al. J. Biol. Chem. 1987; 262:4429-4432.
38. Langer Science 1990; 249:1527-1533.
39. U.S. Pat. No. 5,215,534.
40. U.S. Pat. No. 9,248,242.
41. U.S. Pat. No. 9,427,531.
42. U.S. Pat. No. 9,566,395.
43. U.S. Pat. No. 6,629,949.
44. U.S. Pat. No. 6,659,982.
45. Meehan et al., J. Controlled Release 1996; 46:107-116.
46. Rose-John et al., J Leukoc Biol. 2006; 80(2), 227-36.
47. Committee for Medicinal Products for Human Use, Assessment Report, Apr. 27, 2017 EMA/292840/2017, available at www_dot_emadoteuropa_dot_eu/documents/assessment_report/kevzaraeparpublic_asse ssment_report-t_en_dotpdf.

The invention claimed is:

1. A method for treating or reducing non-inflammatory pain (NIP) in a subject in need thereof, comprising administering to a subject determined to have rheumatoid arthritis and NIP a therapeutically effective dose of an antibody that specifically binds IL-6 receptor, wherein the antibody comprises three heavy chain complementarity determining regions (HCDRs) of a heavy chain variable region comprising an amino acid sequence of SEQ ID NO:1 and three light chain CDRs (LCDRs) of a light chain variable region comprising an amino acid sequence of SEQ ID NO:2, wherein the NIP is defined by a difference between a tender joint count (TJC) and a swollen joint count (SJC) of greater than or equal to 7 (TJC−SJC≥7), and wherein the therapeutically effective dose is effective to treat or reduce the NIP in the subject.

2. The method of claim 1, wherein the antibody comprises a heavy chain variable region comprising the amino acid sequence of SEQ ID NO: 1 and a light chain variable region comprising the amino acid sequence of SEQ ID NO: 2.

3. The method of claim 1, wherein:

(i) the subject has a tender joint count of at least 21;

(ii) the subject has moderately to severely active rheumatoid arthritis;

(iii) the subject was previously ineffectively treated for rheumatoid arthritis by administering at least one disease modifying antirheumatic drug (DMARD) different from the antibody;

(iv) the subject is intolerant to one or more DMARDs different from the antibody;

(v) the subject is considered an inappropriate candidate for continued treatment with one or more DMARDs different from the antibody; or (vi) the subject has had an inadequate response to one or more DMARDs different from the antibody.

4. The method of claim 1, wherein:

(i) the antibody is administered subcutaneously;

(ii) the subject is administered a dose of about 150 mg or about 200 mg of the antibody; and/or (iii) the antibody is administered to the subject at least once every two weeks.

5. The method of claim 1, wherein the subject is not administered any other DMARD different from the antibody during a course of administration with the antibody.

6. The method of claim 1, wherein the subject is also administered one or more additional DMARDs different from the antibody during a course of administration with the antibody.

7. The method of claim 6, wherein the one or more additional DMARDs different from the antibody comprise methotrexate.

8. The method of claim 3, wherein the subject has had an inadequate response or is intolerant to one or more DMARDs different from the antibody, wherein the one or more DMARDs comprise methotrexate or a TNF antagonist, wherein the TNF antagonist is optionally selected from: etanercept, infliximab, adalimumab, golimumab and certolizumab pegol.

9. A method for treating non-inflammatory pain (NIP) in a subject in need thereof, comprising:

(i) selecting a subject who has rheumatoid arthritis and NIP, the NIP is defined by a difference between a tender joint count (TJC) and a swollen joint count (SJC) of greater than or equal to 7 (TJC−SJC≥7), and (ii) administering to the subject a therapeutically effective dose of an antibody that specifically binds IL-6 receptor, wherein the antibody comprises three heavy chain complementarity determining regions (HCDRs) of a heavy chain variable region comprising an amino acid sequence of SEQ ID NO:1 and three light chain CDRs (LCDRs) of a light chain variable region comprising an amino acid sequence of SEQ ID NO:2, and wherein the therapeutically effective dose is effective to treat or reduce the NIP in the subject.

10. The method of claim 9, wherein the antibody comprises a heavy chain variable region comprising the amino acid sequence of SEQ ID NO: 1 and a light chain variable region comprising the amino acid sequence of SEQ ID NO: 2.

11. The method of claim 9, wherein:

(i) the subject has a tender joint count of at least 21;

(ii) the subject has moderately to severely active rheumatoid arthritis;

(iii) the subject was previously ineffectively treated for rheumatoid arthritis by administering at least one disease modifying antirheumatic drug (DMARD) different from the antibody;

(iv) the subject is intolerant to one or more DMARDs different from the antibody;

(v) the subject is considered an inappropriate candidate for continued treatment with one or more DMARDs different from the antibody; or (vi) the subject has had an inadequate response to one or more DMARDs different from the antibody.

12. The method of claim 9, wherein:

(i) the antibody is administered subcutaneously;

(ii) the subject is administered a dose of about 150 mg or about 200 mg of the antibody; and/or (iii) the antibody is administered to the subject at least once every two weeks.

13. The method of claim 9, wherein the subject is not administered any other DMARD different from the antibody during a course of administration with the antibody.

14. The method of claim 9, wherein the subject is also administered one or more additional DMARDs different from the antibody during a course of administration with the antibody.

15. The method of claim 14, wherein the one or more additional DMARDs different from the antibody comprise methotrexate.

16. The method of claim 1, wherein the three CDRs of the VH comprise the amino acid sequences of SEQ ID NOs: 3, 4, and 5, respectively, and the three CDRs of the VL comprise the amino acid sequences of SEQ ID NOs: 6, 7 and 8, respectively.

17. The method of claim 1, wherein the antibody comprises a heavy chain comprising an amino acid sequence of SEQ ID NO: 9, and a light chain comprising an amino acid sequence of SEQ ID NO: 10.

18. The method of claim 1, wherein the antibody is sarilumab.

19. The method of claim 1, wherein the administration reduces the NIP in the subject compared to treatment with a TNF antagonist.

20. The method of claim 9, wherein the three CDRs of the VH comprise the amino acid sequences of SEQ ID NOs: 3, 4, and 5, respectively, and the three CDRs of the VL comprise the amino acid sequences of SEQ ID NOs: 6, 7 and 8, respectively.

21. The method of claim 9, wherein the antibody comprises a heavy chain comprising the an amino acid sequence of SEQ ID NO: 9, and a light chain comprising an amino acid sequence of SEQ ID NO: 10.

22. The method of claim 9, wherein the antibody is sarilumab.

23. The method of claim 9, wherein the administration reduces the NIP in the subject compared to treatment with a TNF antagonist comprising adalimumab.

* * * * *